US008719053B2

(12) United States Patent
Showalter et al.

(10) Patent No.: US 8,719,053 B2
(45) Date of Patent: May 6, 2014

(54) LABORATORY INSTRUMENTATION INFORMATION MANAGEMENT AND CONTROL NETWORK

(75) Inventors: Wayne Showalter, Tucson, AZ (US); Alain L. Larson, Tucson, AZ (US)

(73) Assignee: Ventana Medical Systems, Inc., Tucson, AZ (US)

( * ) Notice: Subject to any disclaimer, the term of this patent is extended or adjusted under 35 U.S.C. 154(b) by 2612 days.

(21) Appl. No.: 10/893,725

(22) Filed: Jul. 16, 2004

(65) Prior Publication Data

US 2005/0038676 A1 Feb. 17, 2005

Related U.S. Application Data

(60) Provisional application No. 60/487,998, filed on Jul. 17, 2003.

(51) Int. Cl.
*G06Q 50/22* (2012.01)
(52) U.S. Cl.
USPC .................................. 705/3; 705/2
(58) Field of Classification Search
USPC ..................................... 705/3; 3/3
See application file for complete search history.

(56) References Cited

U.S. PATENT DOCUMENTS

| 4,803,625 | A | * | 2/1989 | Fu et al. ................... 600/483 |
| 4,855,909 | A | | 8/1989 | Vincent et al. |
| 5,025,391 | A | | 6/1991 | Filby et al. |
| 5,216,925 | A | | 6/1993 | Odernheimer |
| 5,316,726 | A | | 5/1994 | Babson et al. |
| 5,392,209 | A | | 2/1995 | Eason et al. |
| 5,401,110 | A | | 3/1995 | Neeley |
| 5,416,029 | A | | 5/1995 | Miller et al. |
| 5,439,649 | A | | 8/1995 | Tseung et al. |
| 5,449,895 | A | | 9/1995 | Hecht et al. |
| 5,529,166 | A | | 6/1996 | Markin et al. |
| 5,561,556 | A | | 10/1996 | Weissman |
| 5,598,295 | A | | 1/1997 | Olofson |
| 5,608,200 | A | | 3/1997 | Le Goff et al. |
| 5,614,415 | A | | 3/1997 | Markin |
| 5,619,428 | A | | 4/1997 | Lee et al. |

(Continued)

FOREIGN PATENT DOCUMENTS

| AU | 2012209030 A1 | 8/2012 |
| CA | 2 326 039 A1 | 5/2002 |

(Continued)

OTHER PUBLICATIONS

"CAE Specification: DCE 1.1 Remote Procedure Call: Document No. C706," section entitled "Universal Unique Identifier" by the Open Group of Berkshire, UK (1997), 13 pgs.

(Continued)

*Primary Examiner* — Valerie Lubin
*Assistant Examiner* — Reginald R Reyes
(74) *Attorney, Agent, or Firm* — Muirhead and Saturnelli, LLC

(57) ABSTRACT

An interface point network (IPN) and a method for communication with a laboratory information system using an IPN, wherein the IPN includes at least one host computer in communication with at least one laboratory instrument, the laboratory information system and an interface point server in communication with the host computer and the laboratory information system, the interface point server being configured to function as a communication interface between the host computer and the laboratory information system in a manner responsive to a predetermined communication protocol.

35 Claims, 9 Drawing Sheets

A: LIS-IPS connectivity
B: IPS-host connectivity

(56) References Cited

U.S. PATENT DOCUMENTS

| | | |
|---|---|---|
| 5,625,706 A | 4/1997 | Lee et al. |
| 5,631,844 A | 5/1997 | Margrey et al. |
| 5,663,545 A | 9/1997 | Marquiss |
| 5,690,892 A | 11/1997 | Babler et al. |
| 5,777,303 A | 7/1998 | Berney |
| 5,793,969 A * | 8/1998 | Kamentsky et al. .......... 709/213 |
| 5,817,032 A | 10/1998 | Williamson, IV et al. |
| 5,828,776 A * | 10/1998 | Lee et al. .................. 382/133 |
| 5,832,514 A * | 11/1998 | Norin et al. ........................ 1/1 |
| 5,842,179 A | 11/1998 | Beavers et al. |
| 5,875,286 A | 2/1999 | Bernstein et al. |
| 5,876,926 A | 3/1999 | Beecham |
| 5,948,359 A | 9/1999 | Kalra et al. |
| 5,961,923 A | 10/1999 | Nova et al. |
| 5,963,368 A | 10/1999 | Domanik et al. |
| 5,985,670 A | 11/1999 | Markin |
| 6,018,713 A | 1/2000 | Coli et al. |
| 6,045,759 A | 4/2000 | Ford et al. |
| 6,055,487 A | 4/2000 | Margery et al. |
| 6,055,575 A * | 4/2000 | Paulsen et al. ............... 709/229 |
| 6,064,754 A | 5/2000 | Parekh et al. |
| 6,066,300 A | 5/2000 | Carey et al. |
| 6,093,574 A | 7/2000 | Druyer-Sanchez et al. |
| 6,096,561 A | 8/2000 | Tayi |
| 6,113,554 A | 9/2000 | Gilcher et al. |
| 6,150,921 A | 11/2000 | Werb et al. |
| 6,198,695 B1 * | 3/2001 | Kirton et al. ................... 368/10 |
| 6,230,142 B1 * | 5/2001 | Benigno et al. .................... 705/3 |
| 6,250,309 B1 | 6/2001 | Krichen et al. |
| 6,330,348 B1 | 12/2001 | Kerschmann et al. |
| 6,352,861 B1 | 3/2002 | Copeland et al. |
| 6,387,653 B1 | 5/2002 | Voneiff et al. |
| 6,440,068 B1 | 8/2002 | Brown et al. |
| 6,442,440 B1 | 8/2002 | Miller |
| 6,493,724 B1 | 12/2002 | Cusack et al. |
| 6,495,106 B1 | 12/2002 | Kalra et al. |
| 6,520,313 B1 | 2/2003 | Kaarakainen et al. |
| 6,535,129 B1 | 3/2003 | Petrick |
| 6,568,596 B1 | 5/2003 | Shaw |
| 6,572,824 B1 | 6/2003 | Ostgaard et al. |
| 6,581,012 B1 | 6/2003 | Aryev et al. |
| 6,599,476 B1 | 7/2003 | Watson et al. |
| 6,600,420 B2 | 7/2003 | Goff et al. |
| 6,615,763 B2 | 9/2003 | Edwards |
| 6,721,615 B2 | 4/2004 | Fava et al. |
| 6,770,487 B2 | 8/2004 | Crosby |
| 6,776,961 B2 | 8/2004 | Lindsey et al. |
| 6,800,249 B2 | 10/2004 | de la Torre-Bueno |
| 6,814,257 B2 | 11/2004 | Kiene et al. |
| 6,890,759 B2 | 5/2005 | Bierre et al. |
| 6,917,696 B2 | 7/2005 | Soenksen |
| 6,919,044 B1 | 7/2005 | Shibata et al. |
| 6,927,779 B2 | 8/2005 | Mannion et al. |
| 6,941,762 B2 | 9/2005 | Felder et al. |
| 7,006,894 B2 | 2/2006 | De la Huerga |
| 7,035,877 B2 | 4/2006 | Markham et al. |
| 7,141,213 B1 | 11/2006 | Pang et al. |
| 7,163,728 B2 | 1/2007 | Finger |
| 7,177,454 B2 * | 2/2007 | McLaren et al. .............. 382/128 |
| 7,226,788 B2 | 6/2007 | De La Torre-Bueno |
| 7,357,298 B2 | 4/2008 | Pokorny et al. |
| 7,382,258 B2 | 6/2008 | Oldham et al. |
| 7,400,983 B2 | 7/2008 | Feingold et al. |
| 7,468,161 B2 | 12/2008 | Reinhardt et al. |
| 7,562,025 B2 | 7/2009 | Mallett et al. |
| 7,584,019 B2 | 9/2009 | Feingold et al. |
| 7,588,728 B2 | 9/2009 | Clark et al. |
| 7,593,787 B2 | 9/2009 | Feingold et al. |
| 7,603,201 B2 | 10/2009 | Feingold et al. |
| 7,657,070 B2 | 2/2010 | Lefebvre |
| 7,660,724 B2 | 2/2010 | Mallett et al. |
| 7,664,656 B2 | 2/2010 | Mallett et al. |
| 7,666,355 B2 | 2/2010 | Alavie et al. |
| 7,678,331 B2 | 3/2010 | Shanafelter |
| 7,688,207 B2 | 3/2010 | Fritchie et al. |
| 7,745,204 B1 | 6/2010 | Aidun et al. |
| 7,754,149 B2 | 7/2010 | Sugiyama |
| 7,850,912 B2 | 12/2010 | Favuzzi et al. |
| 7,860,727 B2 | 12/2010 | Showalter et al. |
| 7,864,380 B2 | 1/2011 | Descour et al. |
| 7,968,051 B2 | 6/2011 | Oonuma |
| 7,996,172 B2 | 8/2011 | Bauer et al. |
| 8,035,485 B2 | 10/2011 | Fritchie |
| 8,062,591 B2 | 11/2011 | Yamamoto |
| 2001/0035962 A1 | 11/2001 | Yundt-Pacheco |
| 2001/0043882 A1 * | 11/2001 | Berger et al. ................... 422/67 |
| 2001/0044761 A1 | 11/2001 | Berger et al. |
| 2002/0013787 A1 | 1/2002 | Pollard et al. |
| 2002/0026331 A1 | 2/2002 | Case |
| 2002/0029156 A1 | 3/2002 | O'Dowd |
| 2002/0030598 A1 | 3/2002 | Dombrowski et al. |
| 2002/0049782 A1 | 4/2002 | Herzenberg et al. |
| 2002/0064881 A1 | 5/2002 | Devlin et al. |
| 2002/0076819 A1 | 6/2002 | Bowman et al. |
| 2002/0098598 A1 | 7/2002 | Coffen et al. |
| 2002/0106314 A1 | 8/2002 | Pelrine et al. |
| 2002/0116132 A1 | 8/2002 | Rhett et al. |
| 2002/0147515 A1 | 10/2002 | Fava et al. |
| 2002/0150450 A1 | 10/2002 | Bevirt et al. |
| 2003/0021728 A1 | 1/2003 | Sharpe, Jr. et al. |
| 2003/0027342 A1 | 2/2003 | Sheridan et al. |
| 2003/0028501 A1 | 2/2003 | Balaban et al. |
| 2003/0047616 A1 | 3/2003 | Mase et al. |
| 2003/0050794 A1 | 3/2003 | Keck |
| 2003/0059764 A1 | 3/2003 | Ravkin et al. |
| 2003/0074223 A1 | 4/2003 | Hickle et al. |
| 2003/0099573 A1 | 5/2003 | Tseung et al. |
| 2003/0099580 A1 | 5/2003 | Pressman et al. |
| 2003/0110178 A1 | 6/2003 | Woods et al. |
| 2003/0120633 A1 | 6/2003 | De La Torre-Bueno |
| 2003/0144981 A1 | 7/2003 | Schrof et al. |
| 2003/0154105 A1 | 8/2003 | Ferguson |
| 2003/0163031 A1 | 8/2003 | Madden et al. |
| 2003/0179445 A1 | 9/2003 | Maenle et al. |
| 2003/0183683 A1 | 10/2003 | Stewart |
| 2003/0203493 A1 | 10/2003 | Lemme et al. |
| 2003/0211630 A1 | 11/2003 | Richards et al. |
| 2003/0215936 A1 | 11/2003 | Kallioniemi et al. |
| 2003/0225477 A1 | 12/2003 | Gilman et al. |
| 2004/0002163 A1 * | 1/2004 | Reinhardt et al. ............. 436/174 |
| 2004/0023320 A1 | 2/2004 | Steiner et al. |
| 2004/0027462 A1 | 2/2004 | Hing |
| 2004/0032430 A1 | 2/2004 | Yung et al. |
| 2004/0033501 A1 | 2/2004 | Lappe et al. |
| 2004/0039607 A1 | 2/2004 | Savitz et al. |
| 2004/0093516 A1 | 5/2004 | Hornbeek et al. |
| 2004/0098206 A1 | 5/2004 | Milliken et al. |
| 2004/0133543 A1 * | 7/2004 | Clubb et al. ................... 709/200 |
| 2004/0172298 A1 | 9/2004 | Cross et al. |
| 2004/0219069 A1 | 11/2004 | Kalra et al. |
| 2004/0228766 A1 | 11/2004 | Witty et al. |
| 2004/0243444 A1 | 12/2004 | Steusloff et al. |
| 2004/0253662 A1 | 12/2004 | Heid et al. |
| 2004/0259111 A1 | 12/2004 | Marlowe et al. |
| 2004/0266015 A1 | 12/2004 | Favuzzi et al. |
| 2004/0267562 A1 | 12/2004 | Fuhrer et al. |
| 2005/0010781 A1 * | 1/2005 | Harper et al. ................. 713/182 |
| 2005/0026148 A1 | 2/2005 | Rexhausen et al. |
| 2005/0026181 A1 | 2/2005 | Davis et al. |
| 2005/0037406 A1 | 2/2005 | De La Torre-Bueno et al. |
| 2005/0038676 A1 | 2/2005 | Showalter et al. |
| 2005/0054083 A1 | 3/2005 | Vuong et al. |
| 2005/0059155 A1 | 3/2005 | Graupner et al. |
| 2005/0060188 A1 | 3/2005 | Valley |
| 2005/0064535 A1 | 3/2005 | Favuzzi et al. |
| 2005/0075544 A1 | 4/2005 | Shapiro et al. |
| 2005/0096869 A1 | 5/2005 | Drager et al. |
| 2005/0123181 A1 | 6/2005 | Freund et al. |
| 2005/0136509 A1 | 6/2005 | Gholap et al. |
| 2005/0158212 A1 | 7/2005 | Yavilevich |
| 2005/0159982 A1 | 7/2005 | Showalter et al. |
| 2005/0165625 A1 | 7/2005 | Ladic et al. |
| 2005/0191214 A1 | 9/2005 | Tseung et al. |
| 2005/0250211 A1 | 11/2005 | Reinhardt et al. |

(56) References Cited

U.S. PATENT DOCUMENTS

| | | |
|---|---|---|
| 2005/0273272 A1 | 12/2005 | Brando et al. |
| 2005/0280574 A1 | 12/2005 | Tafas et al. |
| 2006/0029519 A1 | 2/2006 | Nakaya et al. |
| 2006/0084088 A1 | 4/2006 | Schultz et al. |
| 2006/0085140 A1 | 4/2006 | Feingold et al. |
| 2006/0088940 A1* | 4/2006 | Feingold et al. .............. 436/47 |
| 2006/0099567 A1 | 5/2006 | Muller-Cohn et al. |
| 2006/0105359 A1 | 5/2006 | Favuzzi et al. |
| 2006/0148063 A1 | 7/2006 | Fauzzi et al. |
| 2006/0155487 A1 | 7/2006 | Yundt-Pacheco |
| 2006/0178776 A1 | 8/2006 | Feingold et al. |
| 2006/0178833 A1 | 8/2006 | Bauer et al. |
| 2006/0190185 A1 | 8/2006 | Ford et al. |
| 2006/0199169 A1 | 9/2006 | Lam et al. |
| 2006/0210432 A1 | 9/2006 | Victor |
| 2006/0239867 A1 | 10/2006 | Schaeffer |
| 2006/0257013 A1 | 11/2006 | Ramm et al. |
| 2006/0265133 A1 | 11/2006 | Cocks et al. |
| 2007/0005169 A1 | 1/2007 | Rohnert et al. |
| 2007/0010911 A1 | 1/2007 | Feingold et al. |
| 2007/0010912 A1 | 1/2007 | Feingold et al. |
| 2007/0029342 A1 | 2/2007 | Cross et al. |
| 2007/0053794 A1 | 3/2007 | Perez et al. |
| 2007/0112804 A1 | 5/2007 | DeSimas et al. |
| 2007/0122797 A1 | 5/2007 | De La Torre-Bueno |
| 2007/0124082 A1 | 5/2007 | De La Torre-Bueno |
| 2007/0124084 A1 | 5/2007 | De La Torre-Bueno |
| 2007/0159688 A1 | 7/2007 | Descour et al. |
| 2007/0172100 A1 | 7/2007 | Lefebvre |
| 2007/0196909 A1 | 8/2007 | Showalter et al. |
| 2007/0207490 A1 | 9/2007 | Benfield et al. |
| 2007/0208534 A1 | 9/2007 | Benfield et al. |
| 2007/0217949 A1 | 9/2007 | Mimura et al. |
| 2007/0224699 A1 | 9/2007 | Gates |
| 2007/0245184 A1 | 10/2007 | Benfield et al. |
| 2007/0254277 A1 | 11/2007 | Scrabeck et al. |
| 2008/0006653 A1 | 1/2008 | Dai et al. |
| 2008/0024301 A1 | 1/2008 | Fritchie et al. |
| 2008/0235055 A1* | 9/2008 | Mattingly et al. .............. 705/3 |
| 2008/0307117 A1 | 12/2008 | Muller-Cohn et al. |
| 2009/0155838 A1 | 6/2009 | Hale |
| 2009/0177427 A1 | 7/2009 | Bauer et al. |
| 2009/0254572 A1 | 10/2009 | Redlich et al. |
| 2009/0291427 A1 | 11/2009 | Muller-Cohn et al. |
| 2009/0298132 A1 | 12/2009 | Muller-Cohn et al. |
| 2010/0009460 A1 | 1/2010 | Clark et al. |
| 2010/0021352 A1 | 1/2010 | Trueeb et al. |
| 2010/0063847 A1 | 3/2010 | Eisenberg et al. |
| 2010/0070305 A1 | 3/2010 | Eisenberg et al. |
| 2010/0113288 A1 | 5/2010 | Adey et al. |
| 2010/0123551 A1 | 5/2010 | Fritchie |
| 2010/0126286 A1 | 5/2010 | Self et al. |
| 2010/0167334 A1 | 7/2010 | Williamson, IV |
| 2010/0217620 A1 | 8/2010 | Kippenhan et al. |
| 2011/0047092 A1 | 2/2011 | Taylor |
| 2011/0115610 A1 | 5/2011 | Hughes |

FOREIGN PATENT DOCUMENTS

| | | |
|---|---|---|
| CA | 2688530 | 12/2008 |
| CA | 2699386 | 3/2009 |
| CN | 2881785 Y | 3/2007 |
| DE | 197 41 385 A1 | 4/1998 |
| DE | 199 05 490 A1 | 8/2000 |
| EP | 0 417 006 A2 | 3/1991 |
| EP | 0 424 692 A1 | 5/1991 |
| EP | 0676053 B1 | 8/1997 |
| EP | 1 004 359 A2 | 5/2000 |
| EP | 1 130 377 A1 | 9/2001 |
| EP | 1 190 771 A1 | 3/2002 |
| EP | 1 245 395 A2 | 10/2002 |
| GB | 2475835 A | 6/2011 |
| JP | 54136389 | 10/1979 |
| JP | 63236966 | 10/1988 |
| JP | 4110752 A | 4/1992 |
| JP | 4184170 A | 7/1992 |
| JP | 6094706 A | 4/1994 |
| JP | 6130069 | 5/1994 |
| JP | 11306271 | 11/1999 |
| JP | 200000975 | 1/2000 |
| JP | 2000065842 | 3/2000 |
| JP | 2002132961 | 5/2002 |
| JP | 2002-312361 A | 10/2002 |
| JP | 2003-279582 | 10/2003 |
| JP | 2003-315347 A | 11/2003 |
| JP | 2003-329690 | 11/2003 |
| JP | 2005-182507 A | 7/2005 |
| JP | 2006-099567 A | 4/2006 |
| JP | 2010-217042 A | 9/2010 |
| SU | 1238173 A2 | 9/1984 |
| SU | 1153369 A | 4/1985 |
| WO | WO 94/11838 A1 | 5/1994 |
| WO | WO 94/15270 A1 | 7/1994 |
| WO | WO 94/22580 | 10/1994 |
| WO | WO 96/38707 | 12/1996 |
| WO | WO 97/39888 | 10/1997 |
| WO | WO 99/28724 | 6/1999 |
| WO | WO 99/30167 A1 | 6/1999 |
| WO | WO 99/43855 A1 | 9/1999 |
| WO | WO 99/44743 | 9/1999 |
| WO | WO 00/13588 | 3/2000 |
| WO | WO 00/15021 | 3/2000 |
| WO | WO 00/19897 | 4/2000 |
| WO | WO 00/51058 | 8/2000 |
| WO | WO 00/62035 | 10/2000 |
| WO | WO 00/70490 | 11/2000 |
| WO | WO 01/08040 A1 | 2/2001 |
| WO | WO 01/09618 | 2/2001 |
| WO | WO 01/20532 | 3/2001 |
| WO | WO 01/20532 A2 | 3/2001 |
| WO | WO 01/31333 A1 | 5/2001 |
| WO | WO01/94016 A1 | 12/2001 |
| WO | WO 02/01482 | 1/2002 |
| WO | WO 02/08769 | 1/2002 |
| WO | WO 02/056121 A2 | 7/2002 |
| WO | WO 03/012453 | 2/2003 |
| WO | WO 03/102854 | 12/2003 |
| WO | WO 2004/044687 | 5/2004 |
| WO | WO 2004/057307 A1 | 7/2004 |
| WO | WO 2004/057308 A1 | 7/2004 |
| WO | WO 2004/058404 | 7/2004 |
| WO | WO 2004/058404 A2 | 7/2004 |
| WO | WO 2004/058950 A1 | 7/2004 |
| WO | WO 2004/059284 A2 | 7/2004 |
| WO | WO 2004/059287 A2 | 7/2004 |
| WO | WO 2004/059288 | 7/2004 |
| WO | WO 2004/059288 A2 | 7/2004 |
| WO | WO 2004/059297 | 7/2004 |
| WO | WO 2004/059297 A1 | 7/2004 |
| WO | WO 2004/059441 | 7/2004 |
| WO | WO 2004/059441 A2 | 7/2004 |
| WO | WO 2004/074845 | 9/2004 |
| WO | WO 2005/084263 A2 | 9/2005 |
| WO | WO 2005/093641 A1 | 10/2005 |
| WO | WO 2005/098455 A1 | 10/2005 |
| WO | WO 2005/100948 A1 | 10/2005 |
| WO | WO 2006/019392 A1 | 2/2006 |
| WO | WO 2006/060125 A2 | 6/2006 |
| WO | WO 2006/118888 A1 | 11/2006 |
| WO | WO 2006/119585 A1 | 11/2006 |
| WO | WO 2006/130760 A2 | 12/2006 |
| WO | WO 2007/123879 A2 | 11/2007 |
| WO | WO 2008/156566 A1 | 12/2008 |
| WO | WO 2011/063139 A1 | 5/2011 |

OTHER PUBLICATIONS

Levi, "The Unified Laboratory: from the concept of the 1980's to the laboratory network of 1995," Analusis, 24(1): M25-M27, 1996. English abstract provided.

Andrews, et al., "Automation in the HP Unified Laboratory. Part 2: A Working Example," Laboratory Robotics and Automation, 5(2):65-67, 1993.

(56) References Cited

OTHER PUBLICATIONS

Casis, et al., "Management of urine and biological fluid samples with P.S.M.," Clinical Chemistry, 48(6): A5-A6, 2002.
Bissell, "The impact of total laboratory automation (tla) on a university medical center clinical laboratory," Clinical Chemistry, 47(6):A115, 2001.
Fleisher, "Assessing total laboratory automation: An overview," Clinical Chemistry, 47(S6):S39, 2001.
Felder, "Modular workcells: modern methods for laboratory automation," Clinica Chimica Acta, 278:257-267, 1998.
Burtis, "Recent technological developments and their impact on laboratory automation," Chemical Technology and Health Division, Oak Ridge National Laboratory, Oak Ridge, Tennessee.
Inomata, "Contribution of an Instrument Manufacturer to the Progress of Life Science and the Welfare of Society," Hitachi Rev., 48(3):100-101, 1999.
Martnez et al., "Automation of a Flow Cytometry Clinical and Research Laboratory," Biomedical Sciences Instrumentation, 29: 301-305, 1993.
MacGillavry, "Aspects Informatiques De L'Automatisation D'Un Laboratoire," Rev. Soc. Roy Belge Ing. Ind., 7-8-9:164-167, 169, 1978. English abstract provided.
Igarashi, "A&T Corporation: An Industry Leader in Modular Connectivity for Clinical Laboratories," JALA, 7(5):46-49, 2002.
Goldschmidt, et al., "Design and positioning of a reference information model for clinical laboratories," Laboratory Automation and Information Management, 34(1):1-6, 1999.
Thompson, "Fitting robots with white coats," Laboratory Automation and Information Management, 31(3):173-193, 1996.
Ikeda, et al., "Total Clinical Laboratory Testing System for Laboratory Automation," Hitachi Rev., 41(4):167-172, 1992.
Watanabe, et al., "High speed, multichannel automatic chemical analyzer and data processing," Journal of the Society of Instrument and Control Engineers, 28(7):562-568, 1989. English abstract provided.
Park, et al., "Three-year Experience in Using Total Laboratory Automation System," Southeast Asian J. Trop. Med. Public Health, 33(2):68-73, 2002.
Casis, et al., "Virtual Automation," Clin. Leadersh Manag. Rev., 15:89-91, 2001.
Fujita, et al., "Advances in the clinical laboratory automation system of Akita University Hospital," Rinsho Byori, 114:13-20, 2000.
Kawagoe, et al., "Dawning of laboratory automation; individually constructed automated systems," Rinsho Byori, 114:1-7, 2000. English abstract provided.
Hoffmann, et al., "Concepts for the third generation of laboratory systems," Clin. Chim. Acta, 278:203-216, 1998.
Boyd, et al., "Robotics and the changing face of the clinical laboratory," Clin. Chem 42(12):1901-1910, 1996.
Koontz, "Automation of laboratory urinalysis," Am. Clin. Lab., 15:14-15, 1996.
Huet, et al., "Design and feasibility of a flexible computerized system for the clinical laboratory, based on the IEEE 488 standardized interface," Comput. Biol. Med., 12:233-240, 1982.
Medvick, et al., "Object-oriented data handling system for an automated chemistry laboratory," MEE-3, Robotics Section, MS J580, Las Alamos National Laboratory, Los Alamos, NM, Conference Paper, pp. 630-643.
Andrews, et al., "Automation in the HP Unified Laboratory. Part 1: General Theory and Concepts," Laboratory Robotics and Automation, 5(2):61-64, 1993.
Orth, et al., "Expert system supported information and management system for analytical laboratories," (Forschungsbericht) Kernforschungszentrum Karlsruhe, May 1990, pp. 1-12.
Hollen, et al., "Automating the analytical laboratory via the Chemical Analysis Automation paradigm," Los Alamos National Lb., NM, 10:668-679, 1997.
King, et al., "Intelligent software for laboratory automation," Trend in Biotechnology, 22(9):440-445, 2004.

Manley, et al., "Robotic system for analytical method development with on-line quantification and a graphical interface," Laboratory Robotics and Automation, 11(5):289-298, 1999.
Arutunian, et al., "Flexible software architecture for user-interface and machine control in laboratory automation," BioTechniques, 25:698-705, 1998.
"Laboratory automation with a graphical computing language," Sensors, 8(6):24-27, 1991.
Dodson, et al., "Contaminant analysis automation demonstration proposal," Proceeding of the Human Factors and Ergonomics Society 37th Annual Meeting; Designing for Diversity, 2:1039, 1993.
Zhou, et al., "Object-oriented programming applied to laboratory automation. 3. The standard robot interface protocol for the Analytical Director," Jour. Chem. Inf. and Comput. Sci., 34(3):558-569, 1994.
Columbus, et al., "Integrated blood-collection system as a vehicle into complete clinical laboratory automation," Clin. Chem., 37(9):1548-1556, 1991.
Regeniter, et al., "Windows to the ward: Graphically oriented report forms. Presentation of complex, interrelated, laboratory data for electrophoresis/immunofixation, cerebrospinal fluid, and urinary protein profiles," Clin. Chem. 49(1):41-50, 2003.
Le Neel, et al., "Technologies for implementation of quality assurance in the clinical laboratory," Clin. Chem. Acta, 287(2):103-110, 1998.
Markin, et al. "Laboratory automation: trajectory, technology, and tactics," Clin. Chem. 46(5):764-771, 2000.
Seaberg, et al., "The role of the total laboratory automation in a consolidated laboratory network," Clin. Chem., 46(5):751-756, 2000.
Hawker, et al., "Development of standards for laboratory automation," Clin. Chem. 46(5):746-750, 2000.
Tomar, "Total laboratory automation and diagnostic immunology," Clin. Diagn. Lab. Immunol., 6(3):293-294, 1999.
"Chapter 4: Introduction to Symbologies," The Bar Code Book: A comprehensive guide to reading, printing, specifying and applying bar code and other machine-readable symbols, by Roger C. Palmer, Revised and Expanded Fourth Edition.
Turner, E.; Paszko, C.; Kolva, D., *Implementing a Laboratory Information Management System (LIMS) in an Army Corps of Engineers' Water Quality Testing Laboratory*, Nov. 2001, vol. 6, No. 5, West End, NC, USA, pp. 60-63.
Luciuk, Rodney; Winkleman, Gary E.; Sluser, Mark; Taylor, Patrick A.; Ens, Arnie M, *A laboratory information management system for small to medium sized soil, plant and water testing laboratories*, 2000, vol. 31, No. 11-14, Swift Current, Saskatchewan, Canada, pp. 1965-1972.
Petcher, D.; Lockhart, E.; Firman, R.; Chen, J.; Johnstone, R.; Chaplin, E., *Robotic System for Handling Infectious Clinical and Pre-Clinical Serum Samples*, Dec. 1999, vol. 4, No. 6, Kenilworth, NJ, USA, pp. 68-75.
Farnsworth, Ralph E., *Laboratory Automatic Storage and Retrieval*, 1997, vol. 9, No. 3, Cincinnati, OH, USA, pp. 129-134.
Ferguson, R.L.; Hwang, H.L.; Bishop, C.P.; Blair, R.L.; Cornett, R.L., *BIOPLUS: An eclectic laboratory information management system for the ORNL Radiobioassay Laboratory*, 1992, Washington, D.C., USA, pp. 1-22.
Bailey, Jeffrey, et al., *The Use of Reflexive Rules in a Laboratory. Information System to Document Resident Training in Special Coagulation Testing*, Abstract from *Advancing Practice, Instruction, and Innovation Through Informalities (APIII 2007) Conference*, Cleveland, Ohio, Sep. 9-12, 2007, 1 Page.
Floyd, Alton PhD, et al., *Process Control for Standardization of Multiple-Step Staining Methods*, Abstract from *Advancing Practice, Instruction, and Innovation Through Informalities (APIII 2007) Conference*, Miami, Florida, Sep. 9-12, 2007, 1 Page.
Grimm, Erin MD, et al., *Efficiency and Quality in Pathology-Slide Tracking*, Abstract from *Advancing Practice, Instruction, and Innovation Through Informalities (APIII 2007) Conference*, Seattle, Washington, Sep. 9-12, 2007, 2 Pages.

(56) References Cited

OTHER PUBLICATIONS

Grimm, Erin MD, et al., *Quality and Efficiency in Pathology-Photography*, Abstract from *Advancing Practice, Instruction, and Innovation Through Informalities (APIII 2007) Conference*, Seattle, Washington, Sep. 9-12, 2007, 1 Page.

Brugal, Gerard, et al., *HOME: Highly Optimized Microscope Environment*, 1992 Wiley-Liss, Inc., Cytometry 13: pp. 109-116.

Krief, Bruno, et al., *IMPACT: Integrating Microscopy for Pathology Activities and Computer Technology*, 1993 IEEE, pp. 76-79.

Schmidt, Rodney A., et al., *Integration of Scanned Document Management with the Anatomic Pathology Laboratory Information System*, American Society for Clinical Pathology Am J Clin Pathol 2006: 126: pp. 678-683.

*Misys Laboratory-Smart, Specimen Management, Routing, and Tracking,* Copyright 2002, 2 Pages.

Brugal, Gerard, et al., *HOME Highly Optimized Microscope Environment*, Advances in Medical Informatics, IOS Press, 1992, pp. 161-163.

Botsman, N.E., et al., *Accelerated Method of Histological Specimen Preparation Using Ultrasound*, 7/I 1967, 6 Pagse, English Translation 4 Pages.

U.S. Appl. No. 09/571,989, filed May 16, 2000, Druyer-Sanchez et al.

Japanese Office Action dated Feb. 19, 2013.

\* cited by examiner

LABORATORY INSTRUMENTATION INFORMATION MANAGEMENT AND CONTROL NETWORK

RELATED CASE INFORMATION

This application claims benefit of U.S. Provisional Application No. 60/487,998, filed Jul. 17, 2003.

FIELD OF THE INVENTION

This invention relates generally to data management and more particularly to communicating, managing, brokering and facilitating the replication of data over a system of instruments, computers and interfaces for managing laboratory information.

BACKGROUND OF THE INVENTION

In order to correctly diagnose or confirm the presence of disease in a patient, a physician typically must excise a sample of diseased tissue and have that tissue examined on a microscopic level by a pathologist. Using a plurality of analysis techniques and laboratory instruments, the pathologist will be able to analyze the diseased tissue to identify any structural (or other) changes in cell tissues and organs. In most cases, the pathologist may be able to 1) identify the type of disease, 2) establish a prognosis on the likely progression of the disease, and 3) make a determination as to what therapy might be most effective in curing or treating the disease. As with most diseases, one important element to a successful treatment or cure is the ability of the physician to rapidly and effectively treat the patient before the disease progresses to an incurable state. This requires that the pathologist have the ability to rapidly analyze the tissue sample, diagnose the condition and disseminate this information to the patient's physician, all the while maintaining accuracy and reliability.

Laboratory Information Systems (LIS) are known for management of patient and laboratory information. Such systems typically consist of a server or host computer, a data base and data base management system, and application software for receiving and processing patient information. Known LIS may be "web-enabled" to facilitate access of the system and information over the Internet.

Unfortunately, however, current Laboratory Information Systems tend to lack the ability to manage workflow with certain laboratory instrumentation, such as, for example, an advanced staining instrument. This management includes basic connectivity, data exchange capability and business rules implemented to optimize workflow, costs and efficiencies. As such, there exist several deficiencies in how these instruments are utilized in the laboratory. A significant amount of time and energy is expended replicating tedious functions, such as data entry, labeling and manual entry for report generation. This replication increases the amount of time it takes to process samples by creating a significant bottleneck in laboratory work flow. The tedious nature of these tasks can substantially increase errors and can affect the accuracy of the diagnostic process. The resulting increase in test completion time may allow a localized disease to progress into systemic proportions, such as a localized tumor metastasizing, having a devastating effect on patient prognosis and/or treatment options and results.

One example of how a bottleneck in laboratory work flow may occur is illustrated in FIG. 1. Typically, a pathologist receives a sample for testing, and orders tests 10. Upon receipt of a tissue sample, accessioning and test order information is entered into the LIS by a laboratory technician 12. However, because the LIS is not connected to the laboratory instruments, the accessioning and test order information that was just entered into the LIS needs to be sent to the test laboratory 14 and re-entered into each laboratory instrument that will be used for testing in order to create slide labels 16. This could take a significant amount of time depending on the number of samples and the extent of testing being performed on the samples. Additionally, each time this data entry function is replicated, the possibility of error in the information transfer increases, reducing the accuracy and reliability of the testing procedure.

Another example of how a bottleneck in laboratory work flow may occur is described as illustrated in FIG. 2 and involves the generation of a status report. Again, the pathologist receives the test sample and orders tests 18. Accessioning and test ordering information is entered into the LIS 20, and then such information must be sent to the test lab 22. Then accessioning and test order information has to be entered into a laboratory instrument 24, such as an advanced staining instrument, and a slide label is generated and the laboratory instrument will begin performing the ordered test. In some cases, the pathologist, lab manager and technician may be keenly interested in the progress of the test and thus may desire to monitor the status of the test. Unfortunately however, the lack of data communications between the LIS and the laboratory instruments prevents test status monitoring by precluding the automatic generation of a test status report. As such, in order to check the status of the test the testing must be interrupted 26 and a test status report must be manually generated.

In addition to this lack of connectivity creating a bottleneck in laboratory work flow, the diagnostic capability of the laboratory is also adversely affected due to the reality that current laboratory set-ups do not have the ability to perform many new and advanced features which may substantially increase the timeliness, reliability and accuracy of new and existing tests.

One way to maximize the timeliness, reliability and accuracy of the sample analysis, condition diagnosis and dissemination of information would be to establish a communication connection between the LIS and the laboratory instrumentation. The extent to which the work flow bottleneck or the performance efficiency would be improved thus would be dependent upon the type of connectivity (unidirectional or bidirectional) established between the LIS and the laboratory instrumentation. For example, a unidirectional, or one-way, connection between the LIS and the laboratory instrumentation would allow for test result information to flow, in one direction, between the laboratory instrument and the LIS, thus eliminating duplicate data entry. Similarly, a bidirectional, or two-way, connection between the LIS and the medical laboratory instrumentation would enable new advanced features to be included, such as order entry and tracking, status updates, sample tracking, quality control, College of American Pathologists (CAP) compliance, inventory management and maintenance, all of which would increase performance time, reliability and accuracy.

Unfortunately however, a suitable system management structure does not exist that would allow for effective control between the LIS and automated laboratory instrumentation, such as staining instrumentation, such that the timeliness of the test performance, data analysis, disease diagnosis and information dissemination process is substantially optimized. Additionally, known systems for interconnecting laboratory instrumentation and information systems do not effectively and automatically identify, prioritize and stage specimens to optimize the throughput and utilization of the automatic staining systems. Nor do known systems have the capability to automate the identification, labeling and tracking of specimens and results through the clinical pathology process. Furthermore, known systems are not specifically capable of optimizing the storage, use, and management of the reagents between staining systems necessary for performing the multitude of staining procedures for disease diagnosis.

SUMMARY OF THE INVENTION

The present invention provides a system, comprised of a single point interface, a laboratory information system (LIS), a single or multiplicity of automated laboratory instruments, such as automated staining instruments, and a single or multiple host computers connected into a management system for performing automated staining.

The single point interface, or Interface Point Server (IPS) conforms to an accepted industry communications protocol standard for receiving and governing the communications interface between a LIS, such as a hospital Laboratory Information System, and laboratory instrument(s) in a network, hereinafter referred to as an Interface Point Network (IPN). The IPS includes, among other things, the functionality to receive and process LIS communications in a manner responsive to a predetermined, standardized communication protocol. A mapping function in the IPS facilitates transformation of the standardized LIS communications for communication and processing at other systems in the network. The IPS provides further interface to functionality of systems in the network, according to the invention. The IPN includes at least one host computer communicating with at least one laboratory instrument, such as automated slide staining instrumentation. The IPS is configured to function as a communication interface between the host computer for the lab instrumentation, to communicate with the host(s), manage data to/from the LIS and coordinate operation of one or more instruments connected to the host computer(s).

In further accord with the invention, a method is provided for communication between a LIS and at least one host computer communicating with at least one lab instrument. The method generally comprises the steps of configuring an interface point network (IPN) including an interface point server (IPS) to communicate with the LIS and the at least one host computer. The at least one host computer includes host data communicated with the at least one laboratory instrument. The IPS is configured to broadcast a message across the IPN, wherein the message includes information responsive to data present on the IPS. A determination is made regarding any differences that exist between the host data and the data present on the IPS. Data is updated on at least one of the IPS and the at least one host computer in a manner responsive to at least one of the host data and the data present on said IPS.

Advantages of the system and method according to the invention include provision of an interface that conforms to an accepted industry communications protocol standard that governs the communications interface between the LIS and the laboratory instrument(s). By providing a single point of communication with the LIS, such an interface substantially reduces the existing burden on each host computer to interface individually with the LIS. Additionally, users of networked systems according to the invention have the ability to move/transfer sample protocols around from one host computer system to another. Moreover, such an interface permits users to connect their system host computers with the LIS and allows data entered on one host computer to be used on other networked host computers without the need to enter the same data everywhere.

In an illustrative embodiment wherein the laboratory instrumentation is automatic slide staining instrumentation, communication over the IPN includes information as would be useful for management of reagent use throughout networked automatic slide staining instrumentation in the IPN. The IPN facilitates the ability to optimize and automate the use of multiple laboratory instruments (staining systems) with varying staining protocols, samples and reagents on multiple systems. Reagents and bulk packages used in the staining environment can be registered on any system in the IPN. Reagent dispensers can be freely moved from staining instrument to staining instrument without regard for which host system they were originally registered on. Staining protocols can be edited at one or another host system and used on other host systems in the network. Stain requests and status can be managed remotely, and multiple slides for a given patient can be dispersed throughout a networked lab for testing and then the information is consolidated at the LIS for management, reporting, billing, etc. Most advantageously, the clinical pathology process, from sample preparation, staining through analysis (data collection) and reporting, may be substantially automated with an implementation according to the invention, wherein user passwords and privileges can be set once on one host system and be used securely throughout the lab on other host systems.

Some additional benefit in implementing a fully connected and integrated system extends to encompass the total clinical pathology work flow, as well as providing for logistical and personnel management within the laboratory environment. As automation or assisted data collection extends to the inspection of samples for diagnosis or treatment, results can be incorporated into the electronic laboratory record, transmitted to the LIS and submitted to the EPR. Further, laboratory technician in-service training, instrument and technician QC tests, instrument and technician lock-out (in the event of failed QC) and logistical support (e.g., ordering and inventory of supplies) can be automated—increasing efficiency and efficacy of the laboratory practice.

BRIEF DESCRIPTION OF DRAWINGS

The foregoing and other features and advantages of the present invention will be better understood from the following detailed description of illustrative embodiments, taken in conjunction with the accompanying drawings in which.

DETAILED DESCRIPTION OF THE INVENTION

Figure 1:
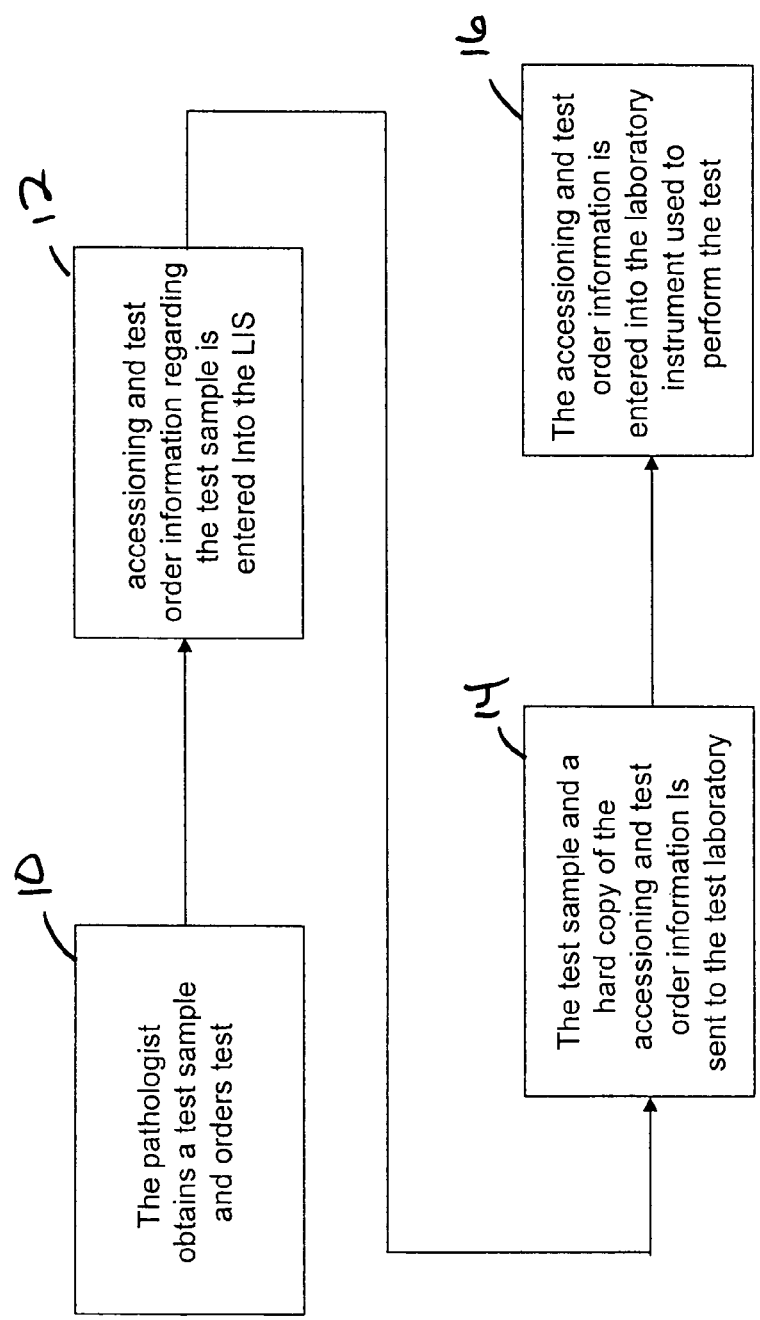
FIG. 1 is a block diagram illustrating a first type of bottleneck in laboratory work flow in accordance with the PRIOR ART.
Figure 2:
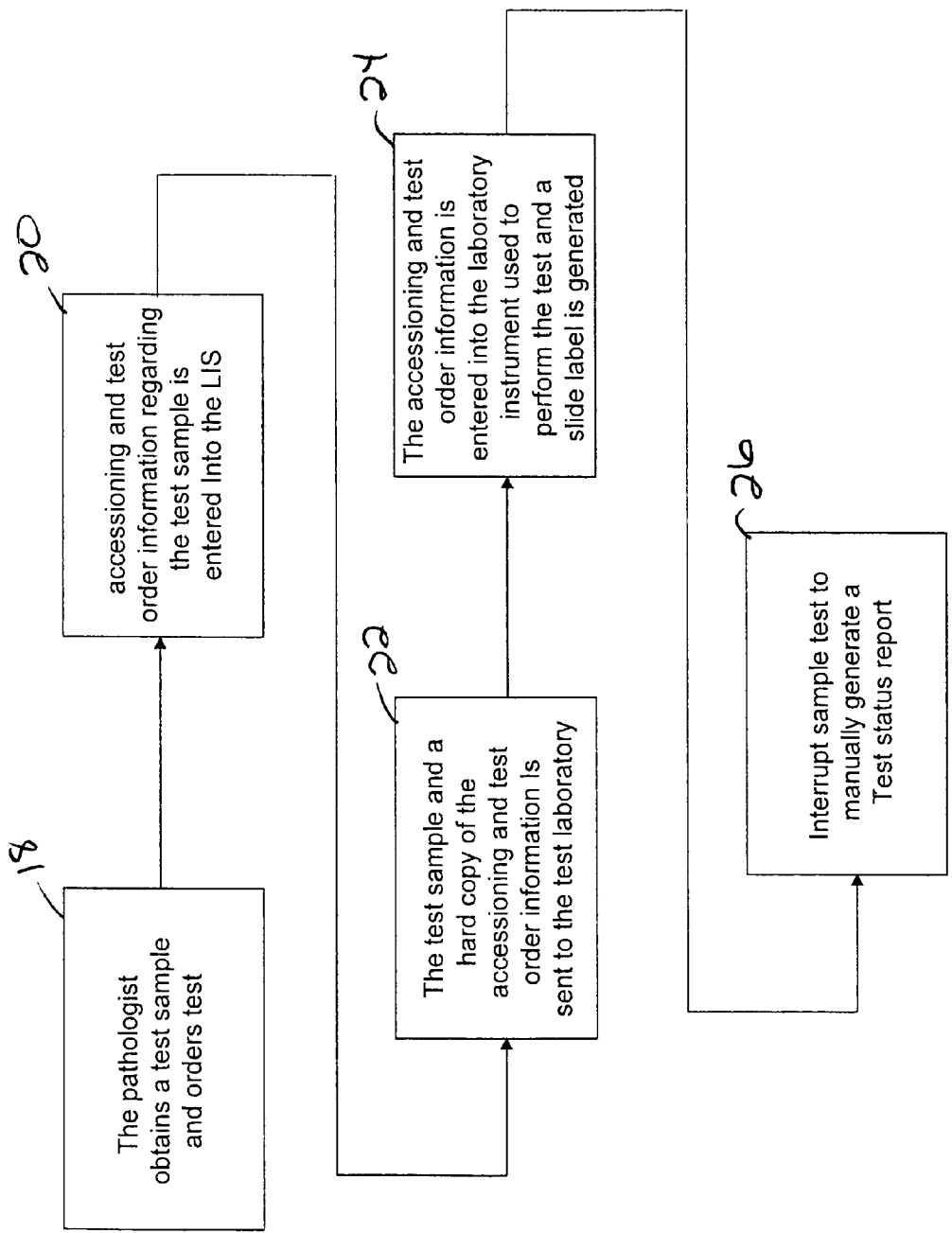
FIG. 2 is a block diagram illustrating a second type of bottleneck in laboratory work flow in accordance with the PRIOR ART.
Figure 3:
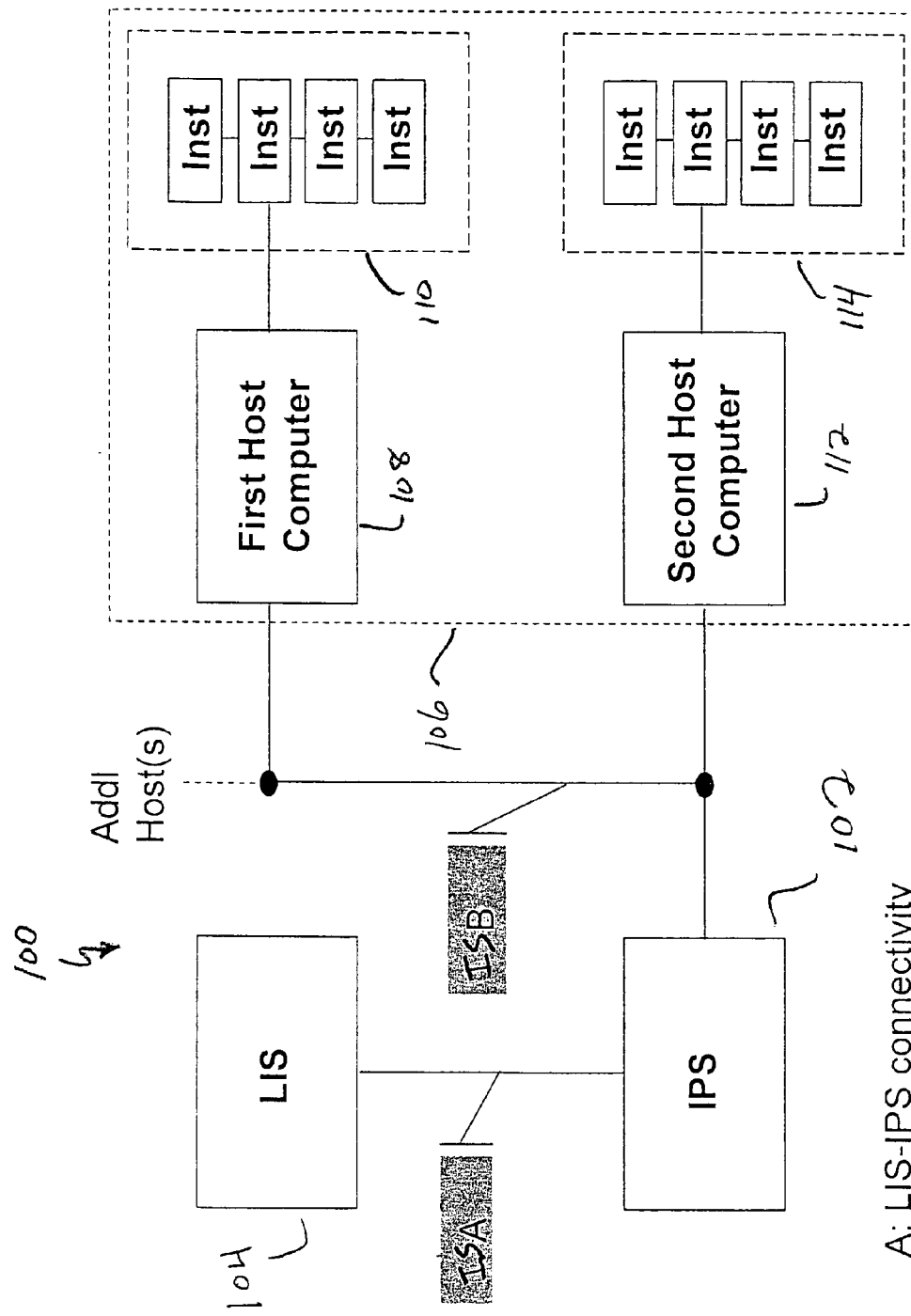
FIG. 3 is a block diagram of an interface point network (IPN) according to an illustrative embodiment of the invention.

Referring to FIG. 3, an Interface Point Network (according to an illustrative embodiment of the invention IPN) 100 is provided and includes an Interface Point Server (IPS) 102 in communication with at least one hospital Laboratory Information System (LIS) 104 and a network of host computers 106. The network of host computers 106 includes a first host computer 108 communicated with a first plurality of laboratory instruments 110 and a second host computer 112 in communication with a second plurality of laboratory instruments 114. The host computer(s) may be interconnected with the laboratory instrumentation via known Ethernet connection or by other interconnectivity mechanisms known in the art, such as known serial or parallel connections or wireless connection. IPS 102 includes Interface Software B (referred to herein synonymously as "ISB" or "Ventana Lab Manager" or "VLM" software), that allows for the performance of automatic functions related to the management of data between network of host computers 106, such as the sharing of data elements between the first host computer 108 and second host computer 112 without difficulty or undesired data transmittal even if the first host computer 108 is one type of host computer and second host computer 112 is a different type of host computer.

The VLM software in the illustrative embodiment runs on the IPS 102. The main purpose of the VLM software is to facilitate the replication of data over a network between host systems. In an illustrative embodiment described herein the host systems are PCs interfaced to known automated slide staining apparatus such as available from Ventana Medical Systems of Tucson, Ariz. The data handled by the VLM can be of many types, such as staining protocols, bar code assignments, reagent dispenser information, reagent ID, reagent consumption, reagent ownership or registration with a particular instrument, user passwords, case data, Patient ID or name, institution, order requestor, accession ID, slide ID, operator ID, operator in-service status, operator quality control (QC) status, instrument QC status, inspection results, diagnosis results and/or staining results. VLM is a piece of software that resides on a PC connected to a network that can provide services to instrument 110, 114 host systems 108, 112. In this embodiment the VLM resides on the IPS 102, however it should be appreciated that the VLM software could reside on one or more of the hosts 108, 112 or be otherwise distributed in the network. Standard TCP/IP protocols are used to connect each instrument host computer with the VLM on the IPS 102. When the VLM software first comes online, it broadcasts a message to all devices on the network proclaiming its presence. If a host is configured to use VLM services, it can then connect with the VLM and request the latest data elements known to the VLM or it can share new data elements with the VLM, making them available to other host computers 108, 112. Typically, in a lab situation, such as in the illustrative embodiment, data sharing among automated slide staining instruments would include: staining protocols; user passwords and privileges; reagents (dispensers/vials); cases; keycodes; templates; panels; and $3^{rd}$ party reagents.

Each host 108, 112 can be independently set up to either share these data elements or not, depending on the individual lab and host requirements. If hosts are sharing data elements, there are algorithms in the software that evaluate which data is the most current, ensuring accurate data replication and avoiding data loss. The VLM initially builds and then holds a copy of the latest data elements being shared by all sharing hosts. It does this with close cooperation of the software in the host systems, which form a partnership with the VLM to make the complete system. Some data elements, most notably reagents, require ownership rights by the host system they are being used on. There is a software messaging system that permits one host to request a transfer of ownership from another host, thereby ensuring that reagent data elements get properly and safely changed (i.e. dispensed amount does not exceed container limits).

The VLM software can manage data from a disparate group of host computers automatically. For instance, Ventana Medical Systems' NexES, HVS and NeuVision hosts can all share data elements between like systems without difficulty or undesired data transmittal from one host type to another. Data element storage and sharing, as described hereinafter, is implemented in the VLM software that allows for new types of hosts, previously unknown to the VLM, to share new types of data elements using the VLM without requiring software upgrades to the VLM system software. This permits host software to be upgraded independently and share new data elements using existing VLM systems. Another function of the VLM is to provide a web interface to a remote operator that can be used for reporting and status updates for the host systems and the instruments to which the hosts are connected.

The IPS 102 implements data element storage and sharing of data that as delivered from a LIS, in the illustrative embodiment described herein, conforms to an adaptation of the Health Level Seven (HL7) standard for information exchange between medical applications, adapted as described hereinafter However, it should be appreciated that other predetermined protocols, such as the IEEE 1073 Standard for Medical Device Communication or proprietary protocols designed for medical device communications, can be implemented according to the invention. As illustrated in FIG. 3, Interface Software A (referred to herein synonymously as "ISA" or "Ventana Interface Point" software or "VIP") also resides on the IPS 102 and acts as a gateway between VLM and a LIS, which in this illustrative embodiment is implementing HL7. The data handled by the VIP includes case management, stain requests from the LIS, staining status and results back to the LIS. Standard TCP/IP protocols are used to connect with the LIS and VLM. Data mapping is available to permit site to site variations in data formats without custom code changes.

The IPS 102 forms the functional connection between the LIS 104 and the IPN, where the IPN is comprised of the IPS 102, host computers and instruments, all connected into a system. The function of the IPS is logically and structurally partitioned into two pieces, the VLM and VIP, as described hereinbefore. While each of these are comprised of contained software objects, it is the encapsulation of their functionality that enable the system to be scalable—for both increased numbers and types of instruments and for function. For the specific application of laboratory automation, it is especially important as the current state of installed instrumentation, types and purposes of data transmission and sharing and levels of automation will be dynamic.

Figure 3A:
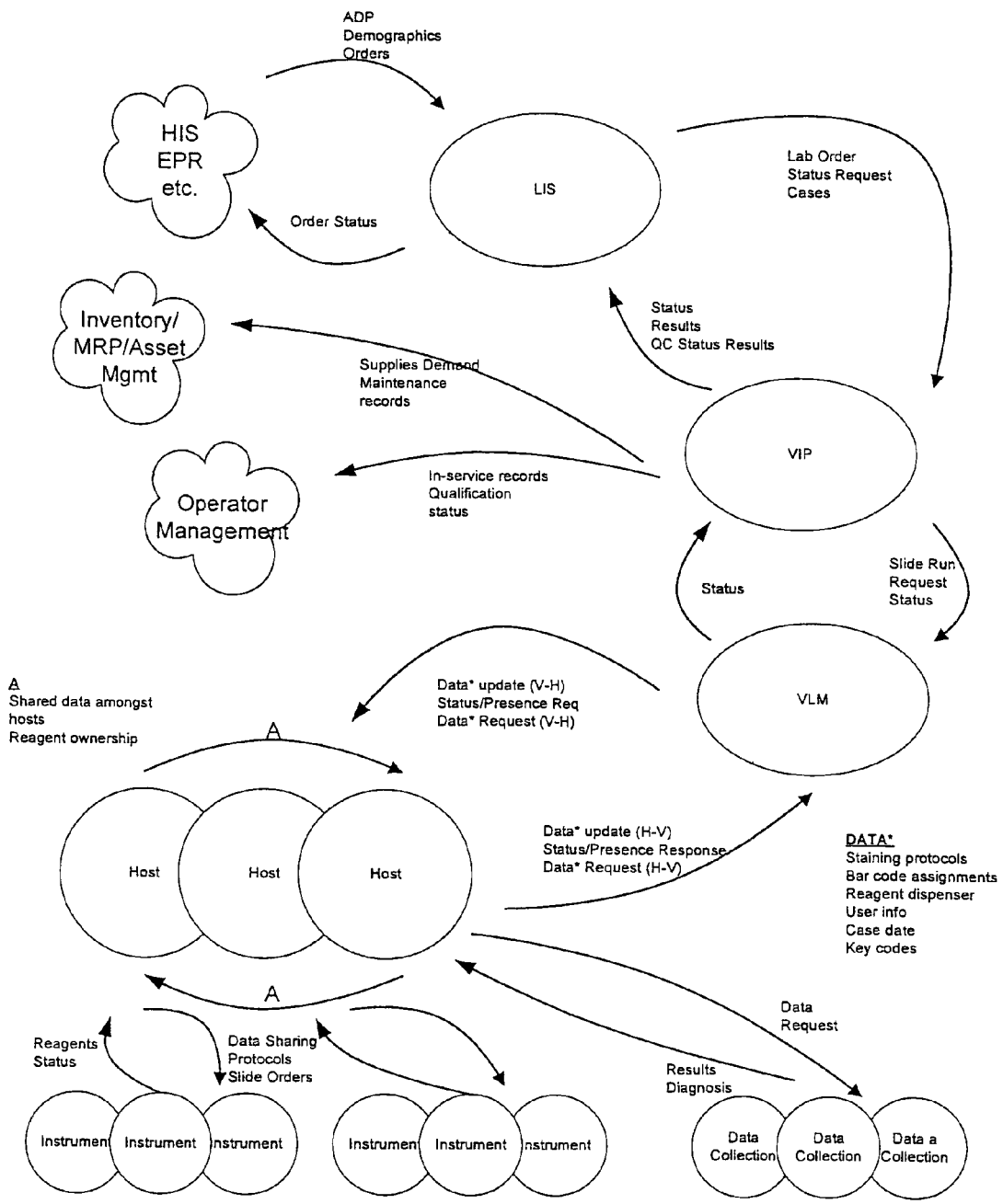
FIG. 3A is a data flow diagram of a system implementing an IPN according to an illustrative embodiment of the invention.

The system according to the invention, therefore, is comprised of hardware entities and software programs that are interfaced through communications protocols and data sharing (generally through the use of databases). In addition to the physical representation of FIG. 3, the system can be represented as a data flow, such as illustrated in FIG. 3a From this perspective, the LIS and other institutional data systems (e.g., HIS, EPR, Inventory management, maintenance management, operator management) represent data resources and management systems that functionally require interaction with the IPN. It is the role of the VIP to provide the gateway interface for this communication with any multiplicity of institutional systems. The advantage of having this encapsulation of function is that it becomes possible to identify and tailor this interface to the needs of a specific site or institution while retaining the key management functions for the IPN in the VLM. In this way, the VIP is the manager for communications to the institution.

Alternately, the VLM provides the functionality to manage the IPN. This set of tasks and their highly unique set of data management and decision processes is encapsulated in the VLM for the purposes of integrating, at an appropriate level, the management functions associated with an entire IPN. Just as a Host is responsible for the management of a single or group of instruments, the VLM must synchronize data, arbitrate staining requests and manage the work flow throughout the IPN. Additionally, the VLM would manage the request and results for the inspection process and ultimately consolidate the laboratory information reporting for a complete order—from initiation through result reporting. Thus the illustrative embodiment provides a multiple tiered architecture, both physical and logical, for the management of workflow, data and status through the laboratory, for example for histology and clinical pathology. It is this tight integration, embodied in the functionally encapsulated modules, that facilitates the adaptation of this system into the highly varied (from site to site) institutional laboratory environment. In illustrative implementations relating to anatomical pathology, the data management method and apparatus according to the invention may be used to manage work flow, including but not limited to, pathology order placement; slide processing optimization on multiple instruments; slide identification through the process; bar code use; reagent use and supply; reagent sharing between laboratory instruments; operator in-service qualification; operator lock out on failure to meet training of QC requirements; laboratory instrument QC testing; and/or laboratory instrument QC lockout on failure to meet QC requirements.

In the illustrative embodiment involving the automation of a clinical pathology process, just as automation of the staining process provides cost, reliability and efficacy advantages over traditional, manual techniques, the automation of the larger clinical pathology process affords similar advantages. In particular, the ability to fully automate the process from sample preparation through result reporting eliminates labor cost, transcription errors, unnecessary data replication and time required to manually report results, as described hereinbefore.

The IPN forms the backbone for providing this level of automation as it has visibility to the order process into the laboratory, the status of an order as it proceeds through the process and can report back results. The ability to consolidate the preparation, processing, inspection and reporting is highly advantageous in obtaining efficiency and accuracy.

Since the VLM manages orders throughout the process, it forms the centerpiece for this integration. The addition of an automated data collection station for inspection (either fully automatic inspection or pathologist driven inspection with automated data collection) provides the next step in fulfilling the full initiation through reporting function. For automated data collection driven by a pathologist inspection, there can be a multiplicity of methods, such as a computer entry station, touch pad data entry, voice data entry, and interactive video with voice. Such data would become part of the clinical record for the specific order.

Referring still to FIG. 3A, the data flow diagram provides visibility at another level to the functional capabilities of the IPN. The data interactions depicted between the LIS and VIP show the high level nature of the interaction. Specifically, the LIS-VLM data flow is focused on IPN system status, staining orders and reporting results. Additionally, those interactions depicted with other non-LIS institutional entities (e.g., inventory and operator management) are related to material and work flow areas impacting the overall institution.

At a lower level (within the system architecture and specifically as between the VLM and hosts and hosts and instruments), the data objects are of a nature allowing for the management of specific aspects of the IPN operation. For example, some specific interactions deal with data sharing between hosts where staining protocols, bar code assignments and user information is exchanged as required to manage the operation and share common data between hosts and instruments.

At a yet lower level, data is shared between hosts to manage specific operating criteria that affect individual instruments. An example of this is reagent ownership, where a particular instrument claims ownership for a specific dispenser. Additionally, the addition of data collection stations to the IPN leverage the data hierarchy design by enabling the allocation and management of orders and reporting of results (which are the critical objects for data collection).

It is this hierarchy, the control exerted by individual entities in the IPN and the appropriate level of data sharing, exchange and storage that provides the efficient partitioning of functionality and data management within the IPN. The model of encapsulating function and associated data at an appropriate level is efficiently applied to this large scale system via the IPN and architecture as described.

Data sharing and storage in (general) is provided one of two ways, relating to the nature of which system entity drives the sharing functions. The ways in which this can occur (for the Host-VLM relationship) is for either the VLM or the host systems to control the active sharing of data over the IPN. In considering an optimal design for sharing and storage, it is critical to consider the nature of the designed functional encapsulation (as discussed hereinbefore with respect to the VIP and VLM as part of the IPS). As a general rule, the entity that has the most 'knowledge' of data requirements is best suited to drive the sharing and storage rules. In the case of the VLM and host computers, the overall detail of function relating to management of reagents and staining recipes is encapsulated in the host computers and consequently, they drive the sharing paradigm from a 'push' perspective—deciding what data is shared and when. In this way, the prioritization and actual actions taken to synchronize data is driven from the use case and represents the more efficient of the means of managing data sharing.

In the case of identifying data that the VLM and VIP may manage, a transition occurs where rather than maintaining a synchronized state, it may be more optimal to simply enable ad hoc transactions or status requests as necessary to support the functionality. In this way, the way in which data is managed changes from a maintained synchronized state to one of identifying and requesting data as required for a specific instance. The use of communications protocols tailored to support such transactions (e.g., HL-7) is highly appropriate for these types of data requirements.

As is known in the art, HL7 is an American National Standards Institute (ANSI) accredited standard that governs the exchange, management and integration of data in order to support clinical patient care and the management, delivery and evaluation of healthcare services. Adaptation and implementation of the HL7 standard, according to the invention, allows new types of data elements to be shared without requiring software upgrades to IPS 102, thus allowing the software on first host computer 108 and second host computer 112 to be upgraded independently while sharing new data elements using existing IPS 102. For example, if first host computer 108 and second host computer 112 are disposed within the network of host computers 106 and are sharing data elements, then in order to avoid data loss the ISB in IPS 102 may include algorithm(s) to ensure that accurate data replication occurs. These algorithm(s) may accomplish this by allowing IPS 102 and network of host computers 106 to work in close cooperation with each other to evaluate which data elements being shared by first host computer 108 and second host computer 112 are the most current and by building and retaining a copy of these data elements. In essence, a "partnership" is formed between network of host computers 106 and IPS 102 and is explained in more detail hereinafter.

It should be appreciated that some data elements, such as those elements regarding reagents in an IPN with automated staining instrumentations, require that the host system have ownership rights to those elements and as such a software messaging system is provided to allow one host computer to marshal these elements, or request a transfer of ownership of these elements, from another host computer. The marshalling of data elements is explained in greater detail hereinafter. This ability to marshal data elements ensures that those data elements that require ownership rights get properly and safely changed to remain within predetermined limits (e.g. dispensed amount does not exceed container limits).

As described briefly above, HL7 is a standard that governs the exchange, management and integration of data between independent applications. As such, HL7 is an open messaging standard governing a method for moving clinical data between independent medical applications. HL7 is designed to enable data communications across a network in real-time, and is described in detail in the HL7 specifications, available from the Health Level Seven organization, Ann Arbor, Mich., which specifications are incorporated herein in the entirety. An implementation of HL7 is used, as described hereinafter, to communicate between the LIS and the single point server IPS 102, and ultimately with the most computer(s) 108, 112 and instruments 110, 114.

Figure 4:
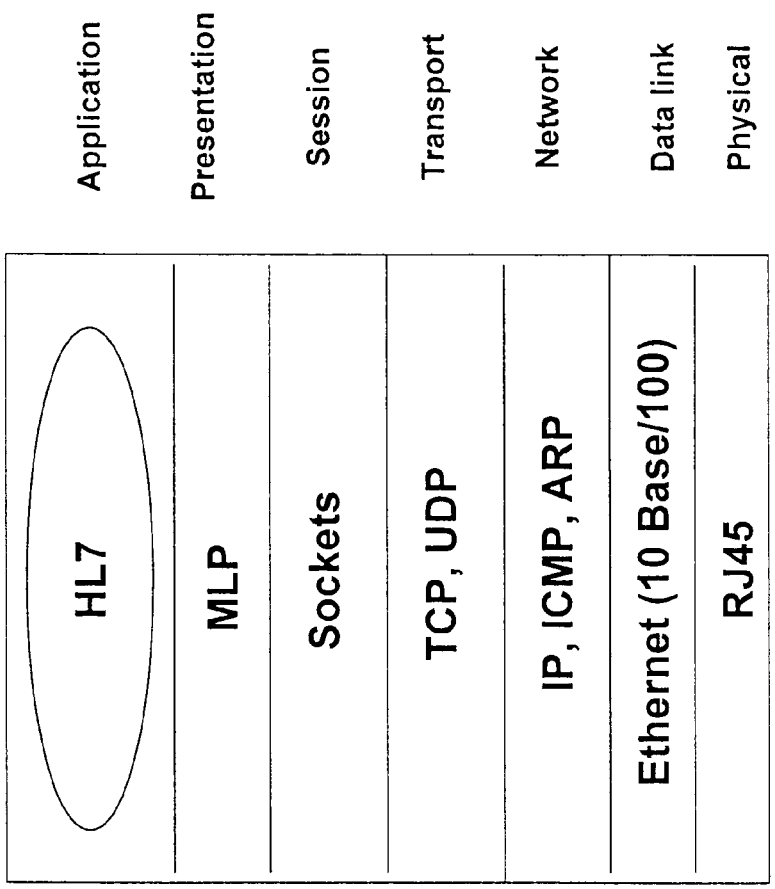
FIG. 4 is a block diagram illustrating a multi-layer software architecture.

Referring to FIG. 4, a high level block diagram illustrating a multi-layer (i.e. seven layer) software architecture is shown and includes a first level or "physical level," a second level or "data link level," a third level or "network level," a fourth level or "transport level," a fifth level or "session level," a sixth level or "presentation level" and a seventh level or "HL7 application level."

Figure 5:
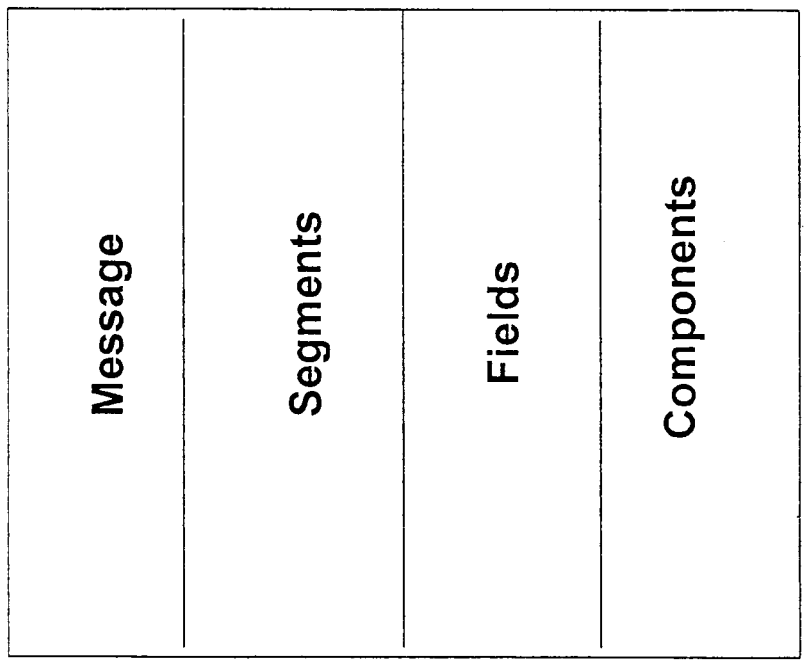
FIG. 5 is a block diagram illustrating an established hierarchy of an HL7 message.

The term "Level Seven" refers to a multi-level (i.e. seven level) software architecture scheme developed by the International Standardization Organization (ISO) and is an application-to-application interface. This means that HL7 defines specification protocols for level 7 functions only (hence, application-to-application interface) and does not define specifications for the remaining six (6) supporting levels. HL7 specifies the type of data to be exchanged, the timing of these communications and the treatment given certain predefined application-specific errors, such as patient demographic information, orders from physicians to the laboratory, test results from the lab to the physician, billing information and enterprise-wide scheduling. FIG. 5 illustrates an additional high level block diagram showing the established hierarchy that governs the construction of an HL7 message and includes a plurality of elements, such as a "components element," a "fields element," a segments element" and a "message element."

The overall HL7 standard is quite broad and supports a central patient care system as well as a distributed environment with departmental data. For example, specific interfaces or messages covered by the standard include patient admissions/registration, discharge or transfer (ADT) information; queries; resource and patient scheduling; orders, status results and clinical observations; billing; master file update information; medical records and patient referral and patient care. Although each of these interfaces or messages may be handled by this standard, for purposes of explanation only the Automatic Test Ordering (OML), Automatic Status Updates (OUL) and Master File Transfer (MFT) messages, as implemented according to the invention in the context of the interface point network, will be addressed in this detailed description. Each of these messages are described separately below.

It should be appreciated that the term "message," as used herein, refers to a group of segments in a defined sequence, the message is the atomic unit of data transferred between systems and each message has a message type that defines its purpose. Similarly, the term "trigger events" refer to real-world events that initiate a message. The trigger event is a code that represents a value, such as an order event and involves a one-to-many relationship between message types and trigger event codes. Thus, although a trigger event code may be associated with only one message type, a message type may be associated with multiple trigger event codes. Moreover, the term "extraneous message segments" refer to those segments that are "Ignored" or "Not Used." Although it is preferred that Ignored or Not Used message segments are not included in an HL7 message, it is not a requirement. As such, when present no data validation is performed on Ignored message segments.

Automatic Test Ordering Message

The ordering message, or Automatic Test Ordering (OML) message, is a unidirectional message used to send accessioning information and test orders from the LIS to the laboratory instrument. The OML message applies to new orders and may not be used to cancel or modify existing orders. The OML message typically includes a plurality of key message segments that include a Message Header (MSH) segment, a Patient Identification (PID) segment, a Patient Visit (PV1) segment, a Specimen and Container (SAC) segment for information relating to the tissue sample, a Common Order (ORC) segment for adding new test orders, an Observation Request (OBR) segment to allow the LIS to request an order and a Message Acknowledgement (MSA) segment to allow for the receipt of any sent messages. The MSH segment, SAC segment, ORC segment and OBR segment are required fields and must contain valid information. The PV1 segment is optional and may or may not include information and the PID segment is a conditional field which is required only if the PV1 segment is completed.

---

Example of an OML Test Order Message

MSH|^~\&|MFN|LIS_APP|APLAB|VIP|APLAB|2002120211
    26||OML^O21|MSG03219|P|2.4|<cr>
PID|||112234^^^METRO HOSPITAL~98223^^^SOUTH
    LAB||Everyman^Adam||19600614|M||C|2101
    Webster # 106^^Oakland^CA^94612|

Example of an OML Test Order Message

```
PV1||O|||||0148^ADDISON,JAMES|0148^ADDISON,JAME
   S|0148^ADDISON,JAMES|AMB||||||0148^ADDISON
   ,JAMES|S|1400|A|||||||||||||||||GENHOS|||
   |||<cr>
SAC|||S03-13241A<cr>
ORC|NW|5212498721A|||ID|B~E<CR>
OBR|1|5212498721A||295^DAB
   Paraffin^STAIN|||199807240826|||||||||||||Ser
   gical Specimen<CR>
ORC|NW|S03-00234B^LAB||||| ^^^^^R<CR>
OBR|1|S03-
   00234B^LAB||111^iVIEW^STAIN|||199808101444|
   |||A||||XXX<CR>
SAC||S03-
   00241A^LAB||||SER|19980620081107|U^UNKNOWN<
   cr>
ORC|NW|S03-00241A^LAB||||| ^^^^^R<CR>
OBR|1|S03-
   00241A^LAB||640^AFB^STAIN|||199808101444|||
   |A||||SER<CR>
ORC|NW|S03-00241A^LAB||||| ^^^^^R<CR>
OBR|1|S03-
   00241A^LAB||642^IRON^STAIN|||199808101444||
   ||A||||SER<CR>
```

The SAC segment includes the data necessary to maintain the containers that are being used throughout the Laboratory Automation System and includes three (3) segment attribute fields: an external accession identifier field, an accession identifier field and a container identifier field. The external accession identifier field includes data that is used to identify the laboratory specimen based upon an identifier provided by an outside facility. The accession identifier field includes data that is used to identify the laboratory specimen based upon an identifier provided by the laboratory performing the tests. It should be noted that the accession identifier field may or may not contain data referring to more than one container. The container identifier field includes data that assigns a unique identifier to the container. A container may hold a primary (original) or an aliquot (secondary) sample of that specimen. For a primary sample, this field includes a Primary Container ID and for bar-coded aliquot samples, this field includes an Aliquot Container ID. In the event an aliquot sample is non-bar-coded, this field remains empty or filled with default data.

The ORC segment is used to transmit fields that are common to all requested services and includes six (6) segment attribute fields: an Order Control (ORC-1) attribute field, a Placed Order (ORC-2) attribute field, a Filled Order (ORC-3) attribute field, a Placer Group (ORC-4) attribute field, an Order Status (ORC-5) attribute field and a Response Flag (ORC-6) attribute field.

The ORC-1 attribute field is a required field that determines the function of the order segment and is critical to the operation of both OML and OUL messages. The ORC-1 attribute field includes ORC field values for a New order/service (NW) function, an Order/service accepted & OK (OK) function and an Unable to accept order/service (UA) function. It should be noted that the only valid value in this field for an OML message is NW. The OUL message, however, can have one of two (2) possible values depending on predetermined conditions. If the observation was completed successfully, then the OUL message value should be OK. If the observation was not completed, then the OUL message value should be UA. In this case, the observation segments (OBX) as described below may be examined to determine the cause of the incomplete message. Each order message that defines any type of new order (i.e. ORC-1=NW, OK or UA) requires an ORC/OBR message pair to define each order to the receiving application. This also applies to any other types of orders, with the OBR being replaced by the appropriate order detail segment.

The ORC-2, ORC-3 and ORC-4 attribute fields are optional fields that are typically used to send the sample accession number to the laboratory instrument and are used to identify an individual order. The ORC-2, ORC-3 and ORC-4 attribute fields contain a unique order identifier which is of the Entity Identifier (EI) type, as explained below. It should be noted that although the first component (a string that identifies an individual order) has a suggested, but not required, fifteen (15) character limit, the first component may include any number of characters as defined by the HL7 standard.

The ORC-5 attribute field is an optional field that is used to specify the status of an order, but that does not initiate any action. The ORC-5 attribute field includes five (5) possible values: an "Identifier" (ID) value, an "In Process" (IP) value, an "Order is completed" (CM) value, an "Error, order unable to complete" (ER) value and an "Order is on hold" (HD) value. It should be noted that in some cases it is assumed that the order status always reflects the status as it is known to the sending application at the time the message is sent. It should also be noted that only the filler can originate the value in this field. As such, this field is only valid in the ORL and OUL messages.

The ORC-6 attribute field is an optional field that enables the status update (OUL) and allows the sending application to determine the amount of information to be returned from the filler via one or more OUL messages. The ORC-6 attribute field includes five (5) possible values: a "Report begin of staining run status" (B) value, a "Report end of staining run status" (E) value, a "Report end of imaging run status" (I) value, a null or "Default" (N) value and a "Pointer" (L) value. It should be noted that this field may be repeated with several ID values if multiple OUL messages are desired.

It should be noted that the ORC segment is a required field in an OML message and if an order detail segment is present, the ORC segment is also mandatory in Unsolicited Laboratory Observation (OUL) messages.

The OBR segment is used by the LIS to request an order and includes seven (7) attribute fields: a "Placer Order Number" (OBR-2) attribute field, a "Filler Order Number" (OBR-3) attribute field, a "Universal Service Identifier" (OBR-4) attribute field, an "Observation Data/Time Number" (OBR-7) attribute field, a "Label Template" (OBR-18) attribute field, a "Barcode Text" (OBR-19) attribute field and a "Placer Supplemental Service Information" (OBR-46) attribute field.

The OBR-2 attribute field is a conditional field that is identical to the ORC-2 attribute field and is used to identify an individual order. This field is a special case of the EI field as explained below and is conditional in a manner responsive to whether a placer order number is provided in attribute field ORC-2. For example, if a placer order number is not provided in attribute field ORC-2, then OBR-2 is a required field.

The OBR-3 attribute field is a conditional field that is identical to the ORC-3 attribute field and is used to identify an individual order. This field is a special case of the EI field as explained below and is conditional because it is required only in the OUL message and will be the same value as the ORC-3 attribute field. OBR-3 is assigned by the order filling (receiving) application and identifies an order uniquely among all orders from a particular filling application.

The OBR-4 attribute field is a required field that contains the CE data type of the staining protocol that will be performed on the slide. This is based on local protocols defined on the laboratory instrument and may be used by the laboratory instrument to determine which staining protocol to use on the slide.

The OBR-7 attribute field is a conditional field that contains any clinically relevant date/time of observation and is the data that the laboratory system uses to identify what staining protocol to perform on a slide. This field represents the date and time the specimen was first obtained. This field is conditional because when the OBR is transmitted as part of a report message, this field must be completed and it is transmitted as part of a request, then this field may be ignored.

The OBR-18 attribute field is an optional field that is a user-defined string of text that allows the LIS to specify the name of the template to be use when printing the slide label. If the value in this field is "NO LABEL" then a label is not generated. Moreover, this may be used to print the instrument barcode label using alternative label printing resources. If this attribute is null, then the laboratory instrument may use the default label template to print.

The OBR-19 attribute field is an optional field that is reserved for future use. This field may be used for site defined barcode symbology and barcode text to uniquely identify various items, such as slides in a laboratory. This field may also be used to allow the LIS to inform the laboratory instrument of unique text that is encoded in the barcode that will be encountered when reading the barcode.

The OBR-46 attribute field is an optional field that is used to describe details such as what types of imaging protocols should be done on the slide that received the OBR-4 staining protocol. The OBR-46 field contains supplemental service information sent from a placer system to a filler system for the universal procedure code reported in OBR-4 Universal Service ID. This field may be used to provide ordering information detail not available in other fields in the OBR segment. Multiple supplemental service information elements may also be reported. This field may also be used to request Image Protocols (s) for the slide after it has been stained with the protocol requested in OBR-4.

It should be noted that when observations are successfully completed, the message returned to the placer field(s) may include the order segment (OBR) followed by observation (OBX) segments for each distinct observation generated by the order. The number of such observation segments may be dependent upon the number of individual measurements performed in the process. In the OUL message if the observations cannot be performed, e.g. because the Universal Service Identifier doesn't match a known protocol, the placer will receive an OBR-25-result status equal to X (to indicate that the study was not preformed). In this case, no observation segments will be transmitted.

The MSA segment includes information sent while acknowledging another message and includes six (6) attribute fields: an "Acknowledgement Code" attribute field, a "Message Control ID" attribute field, a "Text Message" attribute field, an "Expected Sequence Number" attribute field, a "Delayed Acknowledgment Type" attribute field and an "Error Condition" attribute field.

The Acknowledgment Code field is a required field and includes an acknowledgment code that may include at least one (1) of following three (3) values: AA (Original mode: Application Accept—Enhanced mode: Application acknowledgement: Accept), AE (Original mode: Application Error—Enhanced mode: Application acknowledgement: Error) or AR (Original mode: Application Reject—Enhanced mode: Application acknowledgement: Reject).

The Message Control ID field is a required field and includes the message control ID of the message that was sent by the sending system. Also, this may allow the sending system to associate this response with the message for which it is intended. The Text Message field is an optional field that further describes an error condition. This text may be printed in error logs or presented to an end user. The Expected Sequence Number is an optional numeric field used in the sequence protocol. The Delayed Acknowledgment type is optional and may be ignored.

The Error Condition field is an optional field that may allow the acknowledging system to use a user-defined error code to further specify AR or AE type acknowledgments. The Error Condition field may include at least one of the following thirteen (13) values: 0, 100, 101, 102, 103, 200, 201, 202, 203, 204, 205, 206 and 207. An Error Condition value of "0" gives an error text message of "message accepted" and indicates success. This is typically used for systems that must always return a status code and is optional, as the AA conveys success. An Error Condition value of "100" gives an error text message of "Segment Sequence Error" and indicates that the message segments were not in the proper order, or that the required segments are missing. An Error Condition value of "101" gives an error text message of "Required Field Missing" and indicates that a required field is missing from a segment. An Error Condition value of "102" gives an error text of "Data Type Error" and indicates that the field contained data of the wrong data type, e.g. an NM field contained "FOO". An Error Condition value of "103" gives an error text of "Table value not found" and indicates that a field of data type ID or IS was compared against the corresponding table, and not match was found.

An Error Condition value of "200" returns an error text message of "Unsupported Message Type" and indicates that the message type is not supported. An Error Condition value of "201" returns an error text message of "Unsupported Event Code" and indicates that the event code is not supported. An Error Condition value of "202" returns an error text message of "Unsupported Processing ID" and indicates that the processing ID is not supported. An Error Condition value of "203" returns an error text message of "Unsupported Version ID" and indicates that the version ID is not supported. An Error Condition value of "204" returns an error text message of "Unknown Key Identifier" and indicates that the ID of the patient, order, etc., was not found. This field may be used for transactions other than additions, e.g. transfer of a non-existent patient. An Error Condition value of "205" returns an error text message of "Duplicate Key Identifier" and indicates that the ID of the patient, order, etc., already exists. This field may be used in response to addition transactions (Admit, New Order, etc.). An Error Condition value of "206" returns an error text message of "Application Record Locked" and indicates that the transaction could not be performed at the application storage level, e.g. database locked. An Error Condition value of "207" returns an error text message of "Application Internal Error" and is a catchall for internal errors not explicitly covered by other codes.

Automatic Status Updates

The status results message, or Automatic Status Updates (Unsolicited Laboratory Observation or OUL) message is also a unidirectional message. However, the OUL is generated by the laboratory instrument and received by the LIS to notify the LIS of the specimen status. The OUL message is a response status message that combines the original order request from the LIS with a status update relating to that order request and includes at least two (2) key segments: an OBX segment which is the status of each component of the diagnostic report and a ZSI segment which includes detailed information about the reagents used in the test.

It should be noted that with the segment types OBX and OBR, almost any clinical report may be constructed as a three level hierarchy, with the PID at the upper level, an order record (OBR) at the next level and one or more observation records (OBX) at the bottom. It should further be noted that one result segment (OBX) is transmitted for each component of a diagnostic report and it permits the communication of substance data (lot, manufacturer, etc.) of the reagents and other substances involved in the generation of analysis results in addition to the results themselves via the ZSI segments.

The Observation (OBX) segments allow for the transfer of information regarding run number, start time, end time and error messages and includes at least five (5) OBX attribute fields: a Set ID (OBX-1) attribute field, a Value Type (OBX-2) attribute field, an Observation Identifier (OBX-3) attribute field, an Observation Sub-ID (OBX-4) attribute field and an Observation Value (OBX-5) attribute field.

The OBX-1 field is a required field that contains the sequence number. The OBX-2 field is a required field that contains the format of the observation value contained in OBX-5 field and may include at least one of the following values: OBX-2=NM indicates a numeric format, OBX-2=ST indicates a string format and OBX-2=TS indicates a time stamp format. The OBX-3 field is a required field that includes at least one unique identifier for the observation. This may reflect the staining protocol value in the ORC-4 field, with the exception that when this observation refers to an imaging result, OBX-3 field may reflect the value of one of the image protocols in the OBR-46 field. The OBX-4 field is a required field that may be used to distinguish between multiple OBX segments with the same observation ID organized under on OBR and may be used to categorize the observation segment. The OBX-4 field may include at least one of the values shown in Table 1:

TABLE 1

Observation Sub

| OBX-4 Value | Description |
|---|---|
| HostID | Host ID of the laboratory instrument providing the service. |
| HostVersion | Software Version of the Providing Host. |
| StainerSerialNumber | Serial number of the laboratory instrument providing the service. |
| StainerEffectiveType | Effective type of the providing laboratory instrument. |
| RunNumber | Host's run number assigned to provided service. |
| RunStartTime | Start time of service run. |
| RunEstimatedTime | Estimated number of minutes run is expected to take. |
| SlidePosition | The position this slide is located on the laboratory instrument. |
| RunCompletedTime | Actual time service run finished. |
| RunTime | Actual number of minutes run took to run. |
| RunError(n) | Run Error Message (n starts at 1 and increment for each successive error message. |

The OBX-5 field is a required field that contains a value observed by the observation producer. OBX-2 (Value Type) contains the data type for this field according to which observation value is formatted.

The Substance Identifier (ZSI) segment contains data necessary to identify the substance (e.g., reagents) used in the production of analytical test results and includes at least ten (10) attribute fields. The combination of these fields uniquely identify the substance and depending upon the manufacturer, all or some of these fields are required. If the analysis requires multiple substances, this segment is repeated for each substance. The ZSI segment allows for the transfer to information regarding the manufacturer of the reagent, the chemical name, the catalogue number, the lot number and expiration and the serial number.

The ZSI segment includes the attribute fields shown in Table 2:

TABLE 2

ZSI Attribute Fields

| ZSI Attribute Field | Description |
|---|---|
| Substance Type | This is a required field that identifies the substance type used for analysis. It is the group that this substance is in, ANTIBODY, REAGENT, PROBE or BULK. |
| Substance Name | This is a required field that identifies the substance name used for analysis. |
| Substance Lot Number | This is a require field that specifies the lot number assigned by the manufacturer during production of the substance. |
| Substance Lot Serial Number/ Container Identifier | This is a required field that specifies the container assigned by the manufacturer during production of the substance. This identifier should be unique within specific lots of the substance. |
| Catalog Number | This is an optional field that specifies the Manufacturer's catalog ordering number. |
| Substance Other Name | This is an optional field that is used to described additional information about the substance. In the case of Antibodies, it will specify the Clone Name. In the case of Probes, it will hold the Probe Label type. In the case of Reagents and Bulk, this field is not used. |
| Substance Manufacturer Name | This is a required field and identifies the manufacturer of the substance. |
| Expiration Date | This is a required field and identifies the expiration date of the substance. |
| Received Date/Time | This is a required field and identifies the date the substance was received. |
| Intended Use Flag | This is an optional field and identifies the manufacturer's intended use of the substance. This field includes at least four valid values including: ASR (Analyte Specific Reagent), IVD (In Vitro Diagnostic (Class 1 Exempt)), 510(K) (Pre-Market 510(K) Cleared) and PMA (Pre-Market Approved). |

Master File Exchange Message

The master file exchange or master file transfer message is also a unidirectional message and includes two (2) types of messages 1) a Master File Change Notification (MFN) message and a Master File Query (MFQ) message. The master file transfer message is generated by the laboratory instrument and received by the LIS to keep master file information synchronized between the two systems.

The MFQ message allows the LIS to query for a group of records in a particular master file. The MRQ message includes two (2) required segments: a Message Header (MSH) segment and a Query Definition (QRD) segment. The QRD segment is used to define a query and includes ten (10) attribute fields as shown in Table 3.

TABLE 3

QRD Attribute Fields

| QRD Attribute Field | Description |
|---|---|
| QRD-1 | This is an optional field that identifies the Query Date/Time. |
| QRD-2 | This field identifies the Query Format Code. |
| QRD-3 | This field identifies the Query Priority. |
| QRD-4 | This is an optional field that identifies the Query ID. |
| QRD-5 | This field identifies the Deferred Response Type. |
| QRD-6 | This field identifies the Deferred Response Data/Time. |

TABLE 3-continued

QRD Attribute Fields

| QRD Attribute Field | Description |
|---|---|
| QRD-7 | This field identifies the Quantity Limited Request. |
| QRD-8 | This field identifies the Who Subject Filter. |
| QRD-9 | This is a required field that identifies the What Subject Filter and describes the kind of information that is required to satisfy the query request. Valid values include: PROTOCOL (Staining Protocols), TEMPLATE (Slide Templates), ANTIBODY (Logged Antibodies), REAGENT (Logged Reagent), PROBE (Logged Probes) and BULK (Logged Bulks) |
| QRD-10 | This field identifies the What Department Data Code. |

The MFQ transaction also includes a Master File Response (MFR) message that includes seven (7) segments: a Message Header (MSH), a Message Acknowledgement (MSA), a Query Definition (QRD), a Master File Identification (MFI), a Protocol Entry (ZVP), a Template Entry (ZVT) and a $3^{rd}$ Party Chemistry Entry (ZSI), wherein all but ZVP and ZVT are required segments.

The MFI segment is typically used to identify the master file and includes five (5) segment attribute fields as shown in Table 4.

TABLE 4

MFI Attribute Fields

| MFI Attribute Field | Description |
|---|---|
| MFI-1 | Master File Identifier - This is a required field of CE type data that identifies the database table being affected. A plurality of values are supported by this field and include: PROTOCOL (Staining Protocols); TEMPLATE (Slide Template), ANTIBODY (Logged Antibodies), REAGENT (Logged Reagents), PROBE (Logged Probes) and BULK (Logged Bulks). |
| MFI-2 | Master File Application Identifier - This is an optional field that defines the optional code for which the application is responsible for maintaining and may include a valid value, such as VIP. |
| MFI-3 | File-Level Event Code - This is an optional field that identifies the file level event code and may include a valid value, such as UPD, where UPD is a file level event code described as Change file records as defined in the record-level event codes for each record that follows. |
| MFI-4 | Entered Date/Time - This is an optional field that identifies the time stamp for file level events. |
| MFI-5 | Effective Date/Time - This field may be ignored because all Master File transactions are posted as effective when they are received. |

The ZVP segment is used to enter master file protocol information and includes three (3) segment attribute fields as shown in Table 5.

TABLE 5

ZVP Attribute Fields

| ZVP Attribute Field | Description |
|---|---|
| ZVP-1 | Staining Protocol Identifier - This is a required field of CE type data that identifies the Name, Number and Platform Type of the Protocol. A plurality of values are supported by this field and include: My Protocol (ID = 255, STAIN); Image Protocol (IMAGE), Protocol 2 (ID = 222, STAIN) and AFB (ID = 640, STAIN). It should be noted that the numeric ID value range should fall between 0 and 999. |
| ZVP-2 | Modified Date/Time - This is a required field that identifies the date this protocol was last modified |
| ZVP-3 | Procedure Name - This is an optional field of ST type data that identifies the Procedure that the specified Protocol is derived from. |

The ZVT segment is used to enter master file template information and includes two (2) segment attribute fields as shown in Table 6. It should be noted that the ZVT segments are only used when the field type in the MFI-1 segment field is set to template.

TABLE 6

ZVT Attribute Fields

| ZVT Attribute Field | Description |
|---|---|
| ZVT-1 | Template Name - This is a required field of ST type data that identifies the Name of the Label Template. |
| ZVT-2 | Entered Date/Time - This is a required field of TS type data that identifies the date this template was last modified |

The ZSI $3^{rd}$ party Chemistry/Substance segments are user-defined segments that are only used when the field type in the MFI-1 segment field are set to ANTIBODY, REAGENT, PROBE or BULK.

The MFN messages are generated to synchronize laboratory instrument protocols, slide label templates and $3^{rd}$ Party Chemistry with other systems and include a Master File message and a Master File Acknowledgment message. The Master File message may be used to accept third party chemistry information that may be used with user-fillable dispensers and includes six (6) segments: a Message Header (MSH) segment, a Master File Identification (MFI) segment, a Master File Entry (MFE) segment, a Protocol Entry (ZVP) segment, a Template Entry (ZVT) segment and a $3^{rd}$ Party Chemistry Entry (ZSI) segment. All of these segments are required with the exception of the ZVP segment and the ZVT segment which are not used during the import procedure.

The Master File Acknowledgment message is used to acknowledge receipt of a Master File message and includes two (2) required segments: a Message Header (MSH) segment, an Acknowledgment (MSA) segment, and one (1) optional segment: an Error (ERR) segment.

The MFE segment is a required segment that repeats several data elements from the ZVP, ZVT and ZC3 segments. The MFE segment is used to indicate the Record-Level Event Code during import and export operations which will indicate whether a record has been added, deleted or updated and includes five (5) segment attribute fields as shown in Table 7.

TABLE 7

MFE Attribute Fields

| MFE Attribute Field | Description |
|---|---|
| MFE-1 | Record Level Event Code - This is a required field of ID type data that defines the record-level event for the master file record identified by the MFI segment and the primary key field in this segment. Valid values for this field include: MAD (Add record to master file), MDL (Delete record from master file) and MUP (Update record for master file). It should be noted that if the file-level event code is "REP" (MFI - 3 replace file), then each MFE segment must have a record-level event code of "MAD" (add record to master file) in this field. |
| MFE-2 | MFN Control ID - This field may contain data of TS type. |
| MFE-3 | Effective Date/Time - This is an optional field of TS type data that identifies the date and time the change took place. |
| MFE-4 | Primary Key Value - This is a conditional field that uniquely identifies the record of the master file (identified in the MFI segment) to be changed (as defined by the record-level event code). This field is required when the value of MFE-1 is equal to MDL or MUP. |
| MFE-5 | Primary Key Value Type - This is a conditional field that contains the HL7 data type of MFE-4. Valid values for this field include: PROTOCOL (Staining Protocols), TEMPLATE (Slide Templates), ANTIBODY (Logged Antibodies), REAGENT (Logged Reagents), PROBE (Logged Probes) and BULK (Logged Bulks). This field is required when the value of MFE-1 is equal to MDL or MUP. |

In an illustrative implementation wherein the lab instruments 110, 114 (FIG. 3) include automated slide staining, in order to provide an editable mechanism to allow received HL7 messages to be transformed and mapped to slide data elements, an editor with a GUI interface is implemented to allow a user to build and test a transform script that consists of rules for processing HL7 messages.

This mechanism provides an object that can both perform routine HL7 message transformations for using a live transform script and also maintain a transform script that is being actively edited and is not live.

The field mapper function resident in the IPS 102 (FIG. 3), revolves around a single object that will: load and hold the live script; permit placing the script in edit mode without losing the live script; permit taking an edited script live; save an edited script; and perform routine HL7 transformations using the live script, modifying the case data as required.

The application running on the illustrative IPS 102 will create a field mapper object when required and will use it primarily to process a received HL7 message, resulting in case data being extracted from the HL7 message as required. The field mapper needs to be very flexible so that it can work with a large variety of HL7 message data structures present at customer sites. To accommodate this, processing of message data is codified in script 'rules' that consist of an interpreted list of instructions to follow to transform the message data into case data. The IPS 102 handles these processing rules. The following are the 9 slide data fields defined in an illustrative case:
1) Template;
2) PatientID;
3) PatientNAME;
4) Institution;
5) Requester;
6) AccessionID;
7) CaseID;
8) BlockID; and
9) SlideID.

In this illustrative embodiment these are the only possible output fields that can be altered during field mapping transformations. However, it should be appreciated that in other implementations other fields may be defined and processed. The purpose of the field mapper is to fill these data fields with the proper data extracted from the HL7 message.

Those skilled in the art will appreciate that there are numerous but finite HL7 fields present in the HL7 message that can contain data to be harvested by the script.

Script Language Components:

The script field mapping language will consist of rules coded into lines in the general form:

<target element>=<source element>

Taken together, slide data fields, HL7 message elements, internal variables and literal strings will be referred to as 'data types'. Data types can be present in script lines as follows:

| Data Type | Target (Target Data Objects) | Source (Source Data Objects) |
|---|---|---|
| Slide Data Field | x | |
| HL7 Message Element | | X |
| Internal Variable | x | X |
| Literal String | | X |

Internal variables are user definable at the time the script is edited and are used to hold results temporarily during script command processing. Internal variables are created automatically when seen and initially have an empty value.

The language editor is the only way that a user can create script commands. This eliminates development of an elaborate parsing engine to handle user-typed script command lines. Even though script commands will be stored in binary format, they will be presented in a format that makes it easy for a user to view. (This displayed format is used below when discussing syntax of the special functions, even though parsing is not required of the command lines presented.)

COPY Special Function

This function is used to copy the entire contents of one data object and save it to another. The syntax is as follows:

[target data object]=COPY([source data object])

Examples:

If x='1234'

[s]=COPY([x])

results in '1234'

EXTRACT Special Function

This function is a very flexible string extraction function that can be used to mine delimited data from a source data object. Extraction is done using a defined delimiter string and a starting and ending delimiter count. This function allows data to be extracted in various ways such as the left-most, right-most or mid-string. Extraction starts from characters beginning with the starting instance count of the delimiter string, excluding the actual starting delimiter string. Extraction ends with the ending instance count of the delimiter, not including the actual ending delimiter string.

The syntax is as follows:
[target data object]=EXTRACT([source data object], delimiter string, starting index count, ending instance count)
Delimiter strings can be any non-blank string the user types in.
Starting and ending index counts can be any positive integer value. Delimiter counts of 0 have special meaning and depend on where they are found. When a 0 is found in the starting instance count this means to start the extraction from the start of the data object. When a 0 is found in the ending instance count this means to end the extraction at the end of the data object. In other words, using 0 for a starting instance count means take the left part of the data object, which using 0 for a ending instance means to take the right side of the data object.
Examples:
   [x]=EXTRACT(['1234-567-1111-9999'], '-', 1, 2)
      results in '567'
   [x]=EXTRACT(['1234-567-1111-9999'], '-', 1, 3)
      results in '567-1111'
   [x]=EXTRACT(['1234-567-1111-9999'], '-', 0, 2)
      results in '1234-567'
   [x]=EXTRACT(['1234-567-1111-9999'], '-', 1, 0)
      results in '567-1111-9999'
   [x]=EXTRACT(['1234-567-1111-9999'], '-', 0, 0)
      results in '1234-567-1111-9999'
      (which is the whole field, actually)
CONCAT Special Function
This function is used to concatenate multiple source data objects together to make a long string to assign to the target data object. The syntax is as follows:
[target data object]=CONCAT([source data object 1], [source data object 2], [source data object 3], [source data object 4])
There can be 1-4 source data objects; 3-4 are optional. The contents of the source data objects are simply concatenated together to form the result. If more than 4 source data objects need to be concatenated together, an interim result could be stored in an internal variable and more CONCAT commands could follow to continue the concatenation.
Examples:
If x='1234', y='567', z='1111'
[s]=CONCAT([x], ['-'], [y])
   results in '1234-567'
[s]=CONCAT([s], ['-'], [z])
   results in '1234-567-1111'
LEFT Special Function
This function is used to extract a certain amount of characters from the left side of the data object. The syntax is as follows:
[target data object]=LEFT([source data object], # characters)
Examples:
If x='1234'
[s]=LEFT([x], 3)
   results in '123'
RIGHT Special Function
This function is used to extract a certain amount of characters from the right side of the data object. The syntax is as follows:
[target data object]=RIGHT([source data object], # characters)
Examples:
If x='1234'
[s]=RIGHT([x], 3)
   results in '234'

MID Special Function
This function is used to extract a certain amount of characters from the middle of the data object. The syntax is as follows:
[target data object]=MID([source data object], starting position, # characters)
Starting position is the character position to start extracting characters. The number of characters is how many characters to extract.
Examples:
If x='1234'
[s]=MID([x], 2, 2)
   results in '23'
Data Storage
Field mapping scripts will be stored in binary format on disk, and will be retrieved as required and stored as changed. The file format will not be human readable, by design. There will be data integrity features built into the file format such that data corruption will be apparent upon retrieval from disk so that invalid scripts will be readily identifiable and will not be executed. More specifically, data will be stored in encrypted, autowrapped CodeSafe streams.

Figure 6:
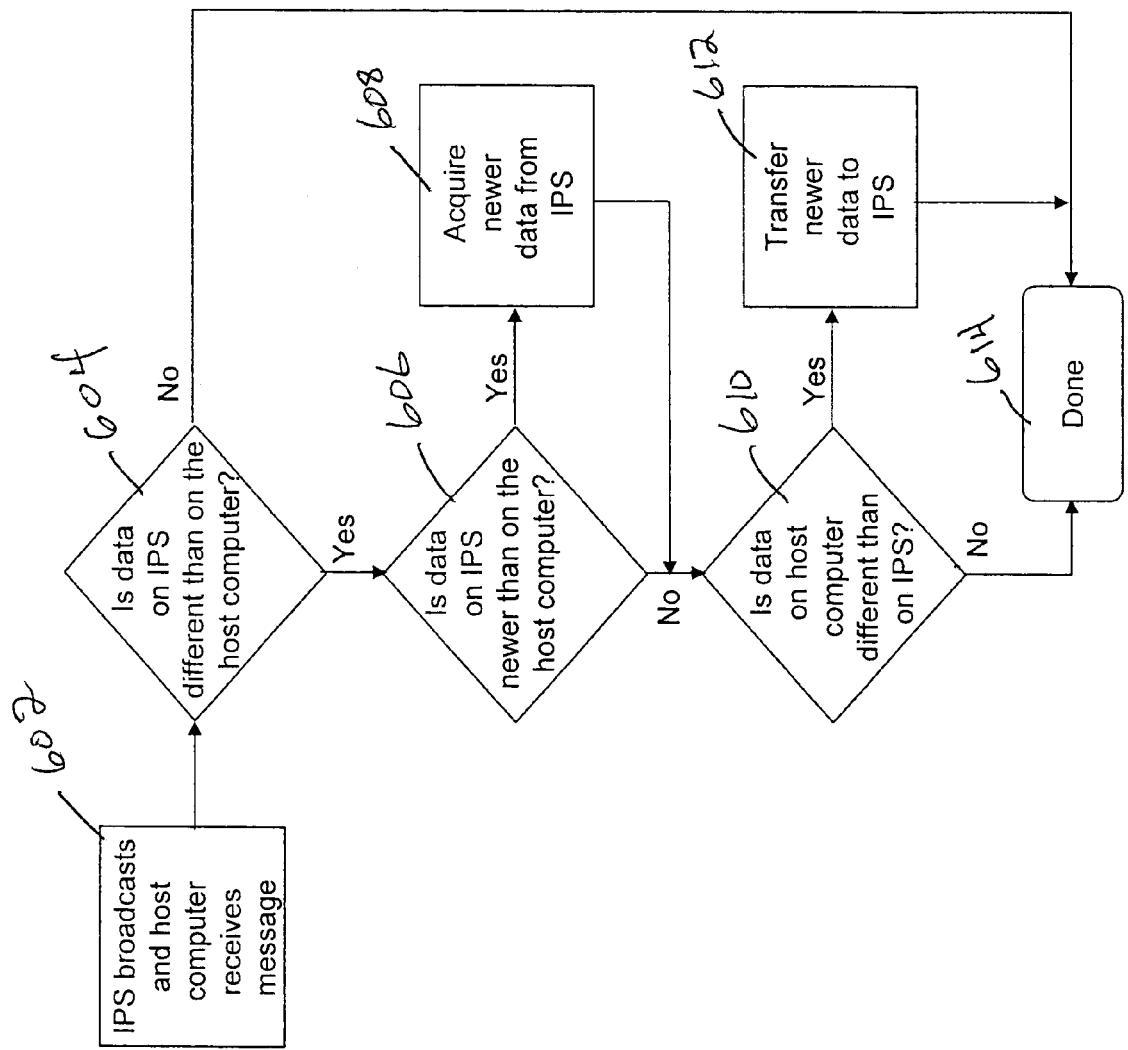
FIG. 6 is a block diagram illustrating a general method of Host/IP Data Synchronization according to an illustrative embodiment of the invention.

Referring now to FIG. 6, a high-level block diagram generally illustrating a host/IP data synchronization method 600 is shown and described as follows, with respect to the IPN illustrated and described hereinbefore with respect to FIG. 3. As described in more detail below, when IPS 102 first connects to IPN 100, IPS 102 begins to periodically broadcast a message to all of the devices on IPN 100, such as first host computer 108 and second host computer 112, to inform each of these devices that IPS 102 has connected to IPN 100, as shown in block 602. This message is of a User Datagram Protocol (UDP) type that is broadcast globally over the entire IPN 100 and includes information on what data is present on IPS 102. It should be appreciated that once IPS 102 connects to IPN 100 any host computer on IPN 100 that is configured to use IPS 102 services may then perform various functions, such as connecting with IPS 102 to request the latest data elements known to IPS 102, or sharing new data elements with IPS 102, thus making them available to network of host computers 106. The type of data that may be shared among instruments in a laboratory situation includes: staining protocols, user passwords and privileges, reagents (dispensers/vials), bulk fluids, cases/keycodes, templates, panels and $3^{rd}$ party reagents. Each host computer in network of host computers 106 may be independently set up to either share or not share data elements, responsive to predetermined conditions, such as individual laboratory and/or computer host requirements.

Upon receiving this broadcast message, network of host computers 106 determines if the data on IPS 102 is different than the data on network of host computers 106, as shown in block 604. This may be accomplished by first host computer 108 comparing the data present on IPS 102 with the data present on first host computer 108 and second host computer comparing the data present on IPS 102 with the data present on second host computer 112. If the data present on both first host computer 108 and second host computer 112 is the same as the data present on IPS 102, then the synchronization process is complete, as show in block 614. However, if the dataset on network of host computers 106 is different from the dataset present on IPS 102, then network of host computers 106 compares its dataset with the dataset present on IPS 102 to determine which dataset is newer. If the dataset on IPS 102 is newer than the dataset on network of host computers 106, then the dataset on network of host computers 106 is replaced by the dataset on IPS 102. However, if the dataset on network of host computers 106 is newer than the dataset on IPS 102, then the dataset on IPS 102 is replaced by the dataset on host of network computers 106.

For example, if the dataset on IPS 102 is different, in whole or in part, from the dataset on first host computer 108, then first host computer 108 determines if its dataset is older than the dataset on IPS 102, as shown in block 606. This may be accomplished by first host computer 108 comparing its dataset with the dataset on IPS 102. If the dataset on first host computer 108 is older than the dataset on IPS 102, then the portion of the dataset on IPS 102 that is newer is acquired by first host computer 108, as shown in block 608. Once this has been accomplished, or if the dataset on first host computer 108 is not older than the dataset on IPS 102, then first host computer 108 determines if its dataset is newer than the dataset on IPS 102, as shown in block 610. As above, this may be accomplished by first host computer 108 comparing its dataset with the dataset on IPS 102. If the dataset on first host computer 108 is newer than the dataset on IPS 102, then the portion of the dataset on host computer 108 that is newer is transferred by first host computer 108 to IPS 102, as shown in block 612. Once this has been accomplished for each host computer on the entire IPN 100, then the synchronization process is complete, as show in block 614.

Figure 7:
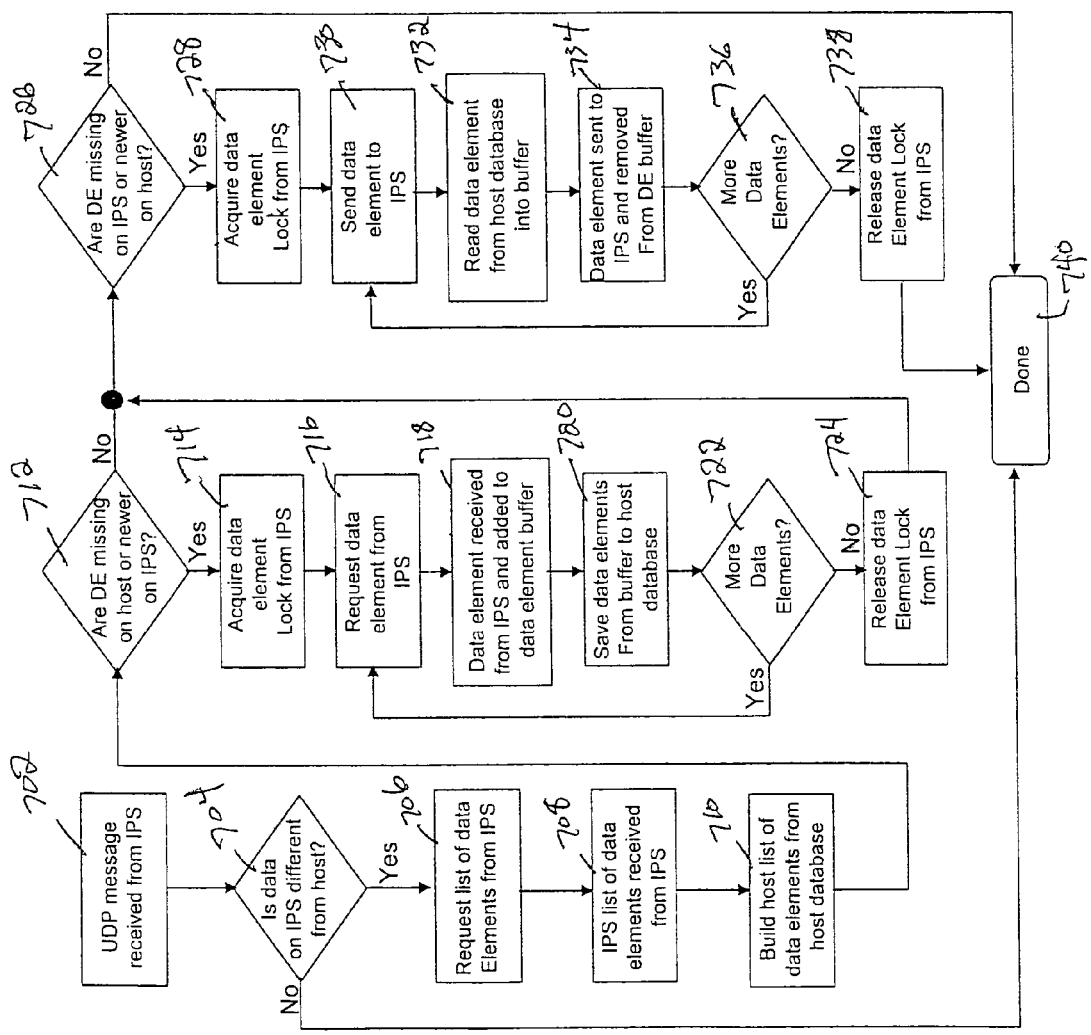
FIG. 7 is a block diagram illustrating a method for Host-Side Data Element Synchronization according to an illustrative embodiment of the invention.

Referring to FIG. 7, a low-level block diagram illustrating a host-side data element synchronization method 700 is shown and described as follows. Although the method of FIG. 7 is described in relation to first host computer 108, it should be appreciated that the method of FIG. 7 applies to each host computer in the plurality of host computers 106. As briefly described above, when IPS 102 first connects to IPN 100, IPS 102 begins to periodically broadcast a UDP message to all of the devices connected to IPN 100 to synchronize the information on all of the devices connected to IPN 100, in this case first host computer 108, as shown in block 702. This UDP message includes an IPS protocol version number as well as information regarding the data present on IPS 102, such as the timestamp or date of that information. When first host computer 108 receives this message, first host computer 108 determines whether its dataset is different from the dataset contained on IPS 102, as shown in block 704. This may be accomplished by comparing the IPS protocol version number contained in the UDP message with the protocol version number on first host computer 108. If the protocol version numbers match then the dataset on IPS 102 is the same as the dataset on first host computer 108 and Host-Side Data Element Synchronization method 700 is completed, as shown in block 740.

However, if the protocol version numbers do not match then the dataset on IPS 102 is different from the dataset on first host computer 108 and first host computer 108 requests the IPS list of data elements (i.e. table of contents) from IPS 102, as shown in block 706. Upon receipt of this request, IPS 102 sends and first host computer 108 receives the IPS list of data elements, as shown in block 708.

First host computer 108 builds a list of host data elements contained on first host computer 108, as shown in block 710 and compares the list of host data elements with the IPS list of data elements to determine if any data elements on first host computer 108 are missing or older than the data elements on IPS 102, as shown in block 712. If there are data elements on first host computer 108 that are missing or older than the data elements on IPS 102, then first host computer 108 requests and acquires a data element lock from IPS 102, as shown in block 714. In the event that there are multiple host computers, this data element lock allows only one host computer, such as first host computer 108, to access the data elements in IPS 102 without having to worry about other host computers simultaneously accessing and changing a particular data element. Once the data element lock has been acquired, first host computer 108 requests IPS 102 to send the data elements in question, as shown in block 716. When first host computer 108 receives the requested data element, first host computer 108 adds the data element to its data element buffer, as shown in block 718. The data element is then saved from the data element buffer to the host database of first host computer 108, as shown in block 720. First host computer 108 then determines if there are any more data elements on first host computer 108 that are missing or older than the data elements on IPS 102, as shown in block 722. If there are, then blocks 716 to 720 are repeated. Otherwise, first host computer 108 sends a request to IPS 102 to release the data element lock, as shown in block 724.

Upon release of the data element lock or if there are no data elements on first host computer 108 that are missing or older than the data elements on IPS 102, then first host computer 108 compares the list of host data elements with the IPS list of data elements to determine if any data elements on IPS 102 are missing or older than the data elements on first host computer 108, as shown in block 726. If there are data elements on IPS 102 that are missing or older than the data elements on first host computer 108, then first host computer 108 requests and acquires a data element lock from IPS 102, as shown in block 728. Once the data element lock has been acquired, first host computer 108 sends the data elements in question to IPS 102, as shown in block 730. First host computer 108 reads the data element from the host database into its data element buffer as shown in block 732 and the data element sent to IPS 102 is removed from the data element buffer, as shown in block 734. First host computer 108 then determines if there are any more data elements on IPS 102 that are missing or older than the data elements on first host computer 108, as shown in block 736. If there are, then blocks 730 to 734 are repeated. Otherwise, first host computer 108 sends a request to IPS 102 to release the data element lock as shown in block 738 and the host-side data element synchronization method 700 is completed, as shown in block 740.

Figure 8:
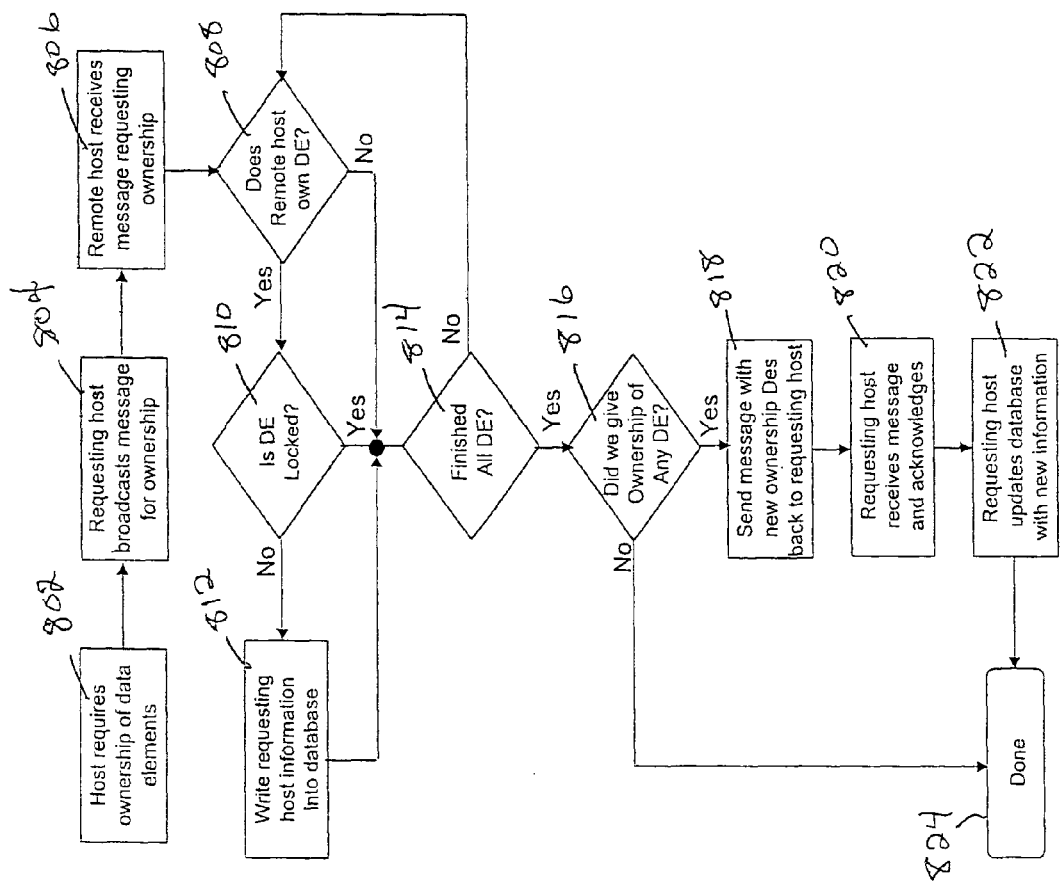
FIG. 8 is a block diagram illustrating a method for Host-Side Data Element Marshalling according to an illustrative embodiment of the invention.

In certain testing situations knowledge of data element location is imperative, such as when dealing with reagents. This situation may be addressed by host side data element marshalling. Referring to FIG. 8, a block diagram illustrating a host-side data element marshalling method 800 is shown and described as follows. When a host computer requires ownership of data elements (e.g. reagents), as shown in block 802, the host computer requests ownership of the data elements by broadcasting a UDP message to IPN 100 requesting ownership of the data elements, as shown in block 804. Each host computer on IPN 100 receives the UDP message, as shown in block 806, and determines if it currently owns the requested data elements, as shown in block 808. The host computer that owns the requested data elements then determines if the requested data element is locked, as shown in block 810. If the requested data element is not locked, then the host computer that owns the requested data element writes information about the requesting host computer into its data element database, including Host ID and Timestamp update, as shown in block 812.

Once this has been completed or if the host computer does not own the requested data element or if the data element is locked, the host computer determines if all requested data elements have been examined for ownership, as shown in block 814. If not, then blocks 808 to 814 are repeated until all requested data elements have been examined for ownership.

If yes, then the host computer determines if ownership of any data elements were transferred to the requesting host computer, as shown in block 816. If not, then host-side data element marshalling method 800 is completed, as shown in block 824. If yes, then the host computer broadcasts the new ownership data elements to the requesting host computer using a UDP message, as shown in block 818. Upon receipt of the new ownership data elements, the requesting host computer sends an acknowledgement message back to the sending host computer, as shown in block 820. The requesting host computer then updates its database with new owner information including incrementing the owner version and resetting the Timestamp, as shown in block 822. Once this has been completed, host-side data element marshalling method 800 is completed, as shown in block 824.

It should be appreciated that this type of direct test ordering performed via HL7 allows for the data entry and labeling functions to be streamlined, thus increasing work flow productivity and quality control. It should further be appreciated that IPS 102 may communicate with LIS 104 and/or network of host computers 106 using standard TCP/IP protocols or any other method suitable to the desired end purpose, such as Internet, Ethernet, Wireless, Local Area Network (LAN), Wide Area Network (WAN), etc. Moreover, the data handled by IPS 102 may be comprised of many types, such as, but not limited to, staining protocols, bar code assignments, reagent dispenser information, user passwords, case management, stain requests from the LIS, staining status and result information sent back to the LIS.

As described above, at least a portion of the methods of FIGS. 6, 7 and 8 may be embodied in the form of computer-implemented processes and apparatuses for practicing those processes. Additionally, at least a portion of methods of FIGS. 6, 7 and 8 may also be embodied in the form of computer program code containing instructions embodied in tangible media, such as floppy diskettes, CD-ROMs, hard drives, or any other computer-readable storage medium, wherein, when the computer program code is loaded into and executed by a computer, the computer becomes an apparatus for practicing the invention. Existing systems having reprogrammable storage (e.g., flash memory) may be updated to implement the invention. It is contemplated that at least a portion of the methods of FIGS. 6, 7 and 8 may also be embodied in the form of computer program code, for example, whether stored in a storage medium, loaded into and/or executed by a computer, or transmitted over some transmission medium, such as over electrical wiring or cabling, through fiber optics, or via electromagnetic radiation, wherein, when the computer program code is loaded into and executed by a computer, the computer becomes an apparatus for practicing the invention. When implemented on a general-purpose microprocessor, the computer program code segments may configure the microprocessor to create specific logic circuits.

It should be appreciated that the network implemented according to the invention may also allow IPS 102 the ability to provide a web interface to remote operators that may be used for reporting and status updates for network of host computer systems 106 and any laboratory instruments, such as first plurality of laboratory instruments 110 and second plurality of laboratory instruments 114.

While the invention has been described with reference to an illustrative embodiment, it will be understood by those skilled in the art that various changes, omissions and/or additions may be made and equivalents may be substituted for elements thereof without departing from the spirit and scope of the invention. In addition, many modifications may be made to adapt a particular situation or material to the teachings of the invention without departing from the scope thereof. Therefore, it is intended that the invention not be limited to the particular embodiment disclosed as the best mode contemplated for carrying out this invention, but that the invention will include all embodiments falling within the scope of the appended claims. Moreover, unless specifically stated any use of the terms first, second, etc. do not denote any order or importance, but rather the terms first, second, etc. are used to distinguish one element from another.

What is claimed is:

1. A laboratory instrument information management and control apparatus, comprising:
    a Laboratory Information System (LIS) configured to manage patient and laboratory information;
    a plurality of laboratory instruments configured to run anatomical pathology tests including automated staining of a sample relating to at least one patient;
    a plurality of host computers, wherein each of said plurality of host computers is in communication with a portion of said plurality of laboratory instruments;
    an interface point server (IPS) in communication with said plurality of host computers and said LIS, said interface point server configured to function as a communication interface between said plurality of host computers and said LIS in a manner responsive to a predetermined communication protocol, and said IPS comprising a first level interface for data communication and control between said LIS and said IPS, and said IPS comprising a second level interface for data communication and control between said plurality of host computers and said IPS, wherein said first level interface and said second level interface are software interfaces, each of said plurality of host computers including host data and being independently configured with data sharing enabled or disabled, said second level interface facilitating replication of data elements shared between said plurality of host computers, said data elements that are shared being stored in a data element storage of said IPS, wherein said second level interface facilitates communicating an update, by a first of said plurality of host computers to a first of said data elements that are shared, to a second of said plurality of host computers sharing said first data element; and
    wherein a first of the plurality of host computers includes a computer readable medium comprising code stored thereon for:
        determining, by said first host computer that said first host computer requires use of a reagent whereby, in order for the first host computer to use the reagent, the first host computer requires ownership of a second data element associated with the reagent;
        sending, by said first host computer to each other host computer of the plurality of host computers, a request requesting ownership of the second data element; and
    wherein each other host computer of the plurality of host computers includes a computer readable medium comprising code stored thereon for:
        receiving, at said each other host computer, the request from the first host computer;
        determining, in accordance with information of a data element database of said each other host computer, whether said each other host computer currently owns the second data element and, if so, whether said second data element is locked; and
        responsive to determining that said each other host computer is current owner of the second data element and the second data element is not locked, updating the data element database of said each other host computer to indicate the first host computer as current owner of the second data element rather than said each other host computer, and sending, by said each other host computer to the first host computer, a message indicating that the first host computer is current owner of the second data element thereby indicating the first host computer as current owner of the reagent associated the second data element.

2. The laboratory instrument information management and control apparatus of claim 1 wherein said plurality of laboratory instruments comprises at least two automated slide staining systems, and said second level interface of said IPS communicates with one of the plurality of host computers for managing data communication and control between said at least two automated slide staining systems and said IPS, and said second level interface of said IPS communicates with said one host computer for managing data communication and control among said at least two automated slide staining systems.

3. The laboratory instrument information management and control apparatus of claim 1 wherein said plurality of laboratory instruments configured to run tests relating to at least one patient includes at least one of said plurality of host computers in communication with a first of said plurality of laboratory instruments as an integral part of said first laboratory instrument.

4. The laboratory instrument information management and control apparatus of claim 1 wherein said predetermined communication protocol governs data exchange, data management and integration of data in accordance with IEEE 1073 standard for Medical Device Communications.

5. The laboratory instrument information management and control apparatus of claim 1 wherein said each of said plurality of host computers is in communication with at least one of said plurality of laboratory instruments via at least one of a wireless connection, a serial connection, a parallel connection and an Ethernet connection.

6. The laboratory instrument information management and control apparatus of claim 1 wherein said LIS is in communication with the interface point server via at least one of an Ethernet connection and an Internet connection.

7. The laboratory instrument information management and control apparatus of claim 1 wherein said plurality of laboratory instruments comprises at least two automated slide staining systems in communication with one of the plurality of host computers, and said second level interface communicates with the one host computer to control data sharing among said at least two automated slide staining systems.

8. The laboratory instrument information management and control apparatus of claim 7 wherein said data sharing among said at least two automated slide staining systems includes sharing data comprising data elements associated with staining protocols; user passwords and privileges; reagent dispensers; reagent vials; cases; keycodes; templates; panels; and $3^{rd}$ party reagents.

9. The laboratory instrument information management and control apparatus of claim 1 wherein said laboratory information system manages the workflow for anatomical pathology in a laboratory, including at least one of pathology order placement; slide processing optimization on multiple instruments; slide identification through the process; bar code use; reagent use and supply; reagent sharing between laboratory instruments; and operator in-service qualification.

10. The laboratory instrument information management and control apparatus of claim 1 wherein said laboratory information system is a hospital laboratory information system.

11. The laboratory instrument information management and control apparatus of claim 1, further comprising:
a computer readable medium of the IPS comprising code stored thereon for broadcasting a message by said second level interface to said plurality of host computers, said message including information regarding said data elements in said data element storage of the IPS;
a computer readable medium, included in each of the plurality of host computers having data element sharing enabled, comprising code stored thereon for performing processing including:
receiving the message broadcast by the second level interface;
determining, using at least a portion of said information included in said message, whether differences exist between host data of said each host computer and said data elements being shared as included in said data element storage; and
if differences exist and include a first difference indicating that either a third data element of the host data is not included in the data element storage of the IPS, or a copy of the third data element of the host data is newer than a copy of the third data element of the data element storage of the IPS, updating the data element storage of the IPS to include the third data element of the host data.

12. A computer implemented method for communication between a laboratory information system and a plurality of host computers comprising the steps of:
configuring an interface point network including an interface point server (IPS) in communication with a laboratory information system and a plurality of host computers managing data and control for a plurality of anatomical pathology laboratory instruments, each of said plurality of host computers including host data and being in communication with a portion of said plurality of laboratory instruments, wherein said interface point server includes a first interface software and a second interface software, wherein each of said plurality of host computers is independently configured with data sharing enabled or disabled, said second interface software facilitating replication of data elements shared between said plurality of host computers, said data elements that are shared being stored in a data element storage of said IPS;
determining, by a first of the plurality of host computers that said first host computer requires use of a reagent whereby, in order for the first host computer to use the reagent, the first host computer requires ownership of a first data element associated with the reagent;
sending, by said first host computer to each other host computer of the plurality of host computers, a request requesting ownership of the first data element;
receiving, at said each other host computer, the request from the first host computer;
determining, in accordance with information of a data element database of said each other host computer, whether said each other host computer currently owns the first data element and, if so, whether said first data element is locked; and
responsive to determining that said each other host computer is current owner of the first data element and the first data element is not locked, updating the data element database of said each other host computer to indicate the first host computer as current owner of the first data element rather than said each other host computer, and sending, by said each other host computer to the first host computer, a message indicating that the first host computer is current owner of the first data element thereby indicating the first host computer as current owner of the reagent associated the first data element.

13. The method of claim 12 wherein the method further includes the step of sharing of data among said plurality of host computers.

14. The method of claim 13 wherein said sharing of data among said plurality of host computers includes sharing data comprising data elements associated with staining protocols; user passwords and privileges; reagent dispensers; reagent vials; cases; keycodes; templates; panels; and $3^{rd}$ party reagents.

15. The method of claim 12 wherein said laboratory information system manages the workflow for anatomical pathology in a laboratory, including at least one of pathology order placement; slide processing optimization on multiple instruments; slide identification through the process; bar code use; reagent use and supply; reagent sharing between laboratory instruments; and operator in-service qualification.

16. The method of claim 12 wherein at least one of said plurality of host computers managing data and control for said plurality of anatomical pathology laboratory instruments is an integral part of a first of said anatomical pathology laboratory instruments.

17. The method of claim 12 wherein said interface point server (IPS) in communication with said laboratory information system communicates via a predetermined communication protocol that governs data exchange, data management and integration of data in accordance with IEEE 1073 standard for Medical Device Communications.

18. The method of claim 12 further comprising:
operating said interface point server to broadcast, by said second interface software, a message across said interface point network, wherein said message includes information regarding data elements in the data element storage of said IPS; and
performing processing by each of said plurality of host computers having data element sharing enabled, said processing including:
receiving the message broadcast by the second interface software;
responsive to said each host computer receiving said message, determining if differences exist between said host data of said each host computer and said data elements in said data element storage of said IPS using information included in said message received; and
if differences exist and include a first difference indicating that either a second data element of the host data of said each host computer is not included in the data element storage of the IPS, or a copy of the second data element of the host data of said each host computer is newer than a copy of the second data element of the data element storage of the IPS, updating said data element storage of said IPS to include the second data element of said host data of said each host computer.

19. The method of claim 18, wherein said message includes a protocol version number associated with a version of data stored at said IPS, said protocol version number being included in said information used in said determining if differences exist between said host data and said data elements in the data element storage of said IPS.

20. A computer implemented method for laboratory instrument information management and control, comprising the steps of:
configuring a Laboratory Information System (US) to manage patient and laboratory information in accordance with a protocol for information exchange between applications;
configuring at least two automated slide staining laboratory instruments to run anatomical pathology tests including automated staining of at least one sample relating to at least one patient;
configuring a plurality of host computers each in communication with at least a portion of said at least two slide staining laboratory instruments;
configuring a server in communication with said plurality of host computers and said LIS, said server comprising a first level interface for data communication and control between said LIS and said server, and said server comprising a second level interface for data communication and control between said at least two automated slide staining laboratory instruments and said server, wherein said server is further configured for data sharing among said plurality of host computers and said at least two automated slide staining laboratory instruments, wherein said first level interface and said second level interface are software interfaces, each of said plurality of host computers is independently configured with data sharing enabled or disabled, said second level interface facilitating replication of data elements shared between said plurality of host computers, said data elements that are shared being stored in a data element storage of said server;
determining, by a first of the plurality of host computers that said first host computer requires use of a reagent whereby, in order for the first host computer to use the reagent, the first host computer requires ownership of a first data element associated with the reagent;
sending, by said first host computer to each other host computer of the plurality of host computers, a request requesting ownership of the first data element;
receiving, at said each other host computer, the request from the first host computer;
determining, in accordance with information of a data element database of said each other host computer, whether said each other host computer currently owns the first data element and, if so, whether said first data element is locked; and
responsive to determining that said each other host computer is current owner of the first data element and the first data element is not locked, updating the data element database of said each other host computer to indicate the first host computer as current owner of the first data element rather than said each other host computer, and sending, by said each other host computer to the first host computer, a message indicating that the first host computer is current owner of the first data element thereby indicating the first host computer as current owner of the reagent associated the first data element.

21. The method for laboratory instrument information management and control of claim 20 wherein said data sharing among said at least two automated slide staining laboratory-instruments-includes sharing data-comprising data elements associated with staining protocols; user passwords and privileges; reagent dispensers; reagent vials; cases; keycodes; templates; panels; and $3^{rd}$ party reagents.

22. The method for laboratory instrument information management and control of claim 20 wherein said laboratory information system manages the workflow for anatomical pathology in a laboratory, including at least one of pathology order placement; slide processing optimization on multiple instruments; slide identification through the process; bar code use; reagent use and supply; reagent sharing between laboratory instruments; and operator in-service qualification.

23. The method of claim 20 wherein said server in communication with said laboratory information system communicates via a predetermined communication protocol that governs data exchange, data management and integration of data in accordance with IEEE 1073 standard for Medical Device Communications.

24. The method of claim 19, wherein said message is received by said first host and said host data is data stored at the first host, and the method further comprising:
comparing said protocol version number with another protocol version number associated with said host data; and
if said comparing determines that said protocol version number is not different than said another protocol version number, determining that said host data and said data elements of said data element storage said IPS are the same.

25. The method of claim 24, wherein, if said comparing determines that said protocol version number is different than said another protocol version number, determining that said host data and said data elements of said data element storage of said IPS are not the same and performing first processing including:
requesting, by said first host, a first list of data elements stored in said data element storage at said IPS;
receiving, by said first host from said IPS, said first list;
building, by said first host, a second list of data elements based on said host data on said first host;
comparing said first list and said second list to determine whether any data elements of said first list are missing from said second list and to determine whether any data elements of said first list are newer than corresponding data elements of said second list;
requesting, by said first host from said IPS, any data elements from said data element storage of said IPS as determined in accordance with said comparing; and
saving, by said first host, any data elements received from said IPS as determined in accordance with said comparing to update said host data of said first host.

26. The method of claim 25, further comprising:
comparing said first list and said second list to determine whether any data elements of said second list are missing from said first list and to determine whether any data elements of said second list are newer than corresponding data elements of first second list; and
sending, by said first host, any data elements to said IPS as determined in accordance with said comparing to update said data elements of said data element storage of said IPS.

27. The method of claim 25, wherein prior to said first host requesting any data elements from said IPS as determined in accordance with said comparing, said first host acquires a data element lock from said IPS.

28. The method of claim 26, wherein prior to said first host sending any data elements to said IPS as determined in accordance with said comparing, said first host acquires a data element lock from said IPS.

29. The method of claim 20, further comprising:
receiving, by said server, a message in accordance with a protocol at an application level;
extracting, by said server, data from said message in accordance with rules including an interpreted list of instructions to map extracted data into data elements; and
periodically broadcasting a message to at least one host in accordance with a transport level protocol of a multi-level software architecture in connection with data synchronization between said at least one host and said server.

30. The method of claim 20, further comprising:
broadcasting a message by said second level interface to said plurality of host computers, said message including information regarding said data elements which are shared and are stored in the data element storage of the server; and
performing processing by each of said plurality of host computers having data element sharing enabled, said processing including:
receiving the message broadcast by the second level interface;
determining, using at least a portion of said information included in said message, whether differences exist between host data of said each host, computer and said data elements being shared as included in said data element storage of the server; and
if differences exist and include a first difference indicating that either a second data element of the host data of said each host computer is not included in the data element storage of the IPS, or a copy of the second data element of the host data of said each host computer is newer than a copy of the second data element of the data element storage of the IPS, updating said data element storage of said IPS to include the second data element of said host data of said each host computer.

31. A computer implemented method for maintaining ownership of a reagent represented by a data element comprising:
associating said reagent with said data element;
determining that a first host requires use of said reagent whereby, in order for the first host to use the reagent, the first host requires ownership of the data element associated with said reagent;
sending, by said first host to each of a plurality of hosts, a request requesting ownership of the data element; and
receiving, by each of said plurality of hosts, said request, and wherein, in response to receiving said request, said each host performs first processing, said first processing including:
determining, in accordance with information of a data element database of said each host, whether said each host currently owns said data element and if so, determining whether said data element is locked; and
responsive to determining that said each host is current owner of said data element and said data element is not locked, updating said data element database of said each host to indicate said first host as the current owner of said data element rather than said each host, and sending, by said each host to said first host, a message to said first host indicating that said first host is the current owner of said data element, the current owner of the data element being indicated as current owner of the reagent associated therewith.

32. The method of claim 31, wherein said updating said data element database includes writing information about the first host, said information written about the first host including a host identifier of the first host and a timestamp of said updating.

33. The method of claim 31, wherein said first processing further comprises:
  receiving, by said first host, said message;
  sending, by said first host to said each host, an acknowledgement message; and
  updating a second data element database of said first host in accordance with said message to record said first host as said current owner of the data element.

34. A non-transitory computer readable medium comprising code stored thereon for communication between a laboratory information system and at least one host computer, the computer readable medium comprising code stored thereon for: configuring an interface point network including an interface point:server (IPS) in communication with a laboratory information system and a plurality of host computers managing data and control for a plurality of anatomical pathology laboratory instruments, each of said plurality of host computers including host data and being in communication with a portion of said plurality of laboratory instruments, wherein said interface point server includes a first interface software and a second interface software, wherein each of said plurality of host computers is independently configured with data sharing enabled or disabled, said second interface software facilitating replication of data elements shared between said plurality of host computers, said data elements that are shared being stored in a data element storage of said IPS;
  determining, by a first of the plurality of host computers that said first host computer requires use of a reagent whereby, in order for the first host computer to use the reagent, the first host computer requires Ownership of a first data element associated with the reagent;
  sending, by said first host computer to each other host computer of the plurality of host computers, a request requesting ownership of the first data element;
  receiving, at said each other host computer, the request from the first host computer; determining, in accordance with information of a data element database of said each other host computer, whether said each other host computer currently owns the first data element and, if so whether said first data element is locked; and
  responsive to determining that said each other host computer is current owner of the first data element and the first data element is not locked, updating the data element database of said each other host computer to indicate the first host computer as current owner of the first data element rather than said each other host compute and sending, by said each other host computer to the first host computer, a message indicating that the first host computer is current owner of the first data element thereby indicating the first host computer as current owner of the reagent associated the first data element.

35. A non-transitory computer readable medium comprising code stored thereon for laboratory instrument information management and control, the computer readable medium comprising code stored thereon for:
  configuring a Laboratory Information System (LIS) to manage patient and laboratory information in accordance with a protocol for information exchange between applications;
  configuring at least two automated slide staining laboratory instruments to run anatomical pathology tests including automated staining of at least one sample relating to at least one patient;
  configuring a plurality of host computers each in communication with at least a portion of said at least two slide staining laboratory instruments;
  configuring a server in communication with said plurality of host computers and said LIS, said server comprising a first level interface for dam communication and control between said LIS and said server, and said server comprising a second level interface for data communication and control between said at least two automated slide staining laboratory instruments and said server, wherein said server is further configured for data sharing among said plurality of host computers and said at least two automated slide staining laboratory instruments, wherein said first level interface and said second level interface are software interfaces, each of said plurality of host computers is independently configured with data sharing enabled or disabled, said second level interface facilitating replication of data elements shared between said plurality of host computers, said data elements that are shared being stored in a data element storage of said server;
  determining, by a first of the plurality of host computers that said first host computer; requires use of a reagent whereby, in order for the first host computer to use the reagent, the first host computer requires ownership of a first data element associated with the reagent;
  sending by said first host computer to each other host computer of the plurality of host computers, a request requesting ownership of the first data element;
  receiving, at said each other host computer, the request from the first host computer;
  determining in accordance with information of a data element database of said each other host computer, whether said each other host computer currently owns the first data element and, if so, whether said first data element is locked; and
  responsive to determining that said each other host computer is current owner of the first data element and the first data element is not locked, updating the data element database of said each other host computer to indicate the first host computer as current owner of the first data element rather than said each other host computer, and sending, by said each other host computer to the first host computer a message indicating that the first host computer is current owner of the first data element thereby indicating the first host computer as current owner of the reagent associated the first data element.

* * * * *